(12) United States Patent
Ashihara et al.

(10) Patent No.: US 8,177,733 B2
(45) Date of Patent: May 15, 2012

(54) BODY WEIGHT SUPPORT DEVICE AND BODY WEIGHT SUPPORT PROGRAM

(75) Inventors: Jun Ashihara, Saitama (JP); Yosuke Endo, Saitama (JP); Yasushi Ikeuchi, Saitama (JP); Yutaka Hiki, Saitama (JP); Toru Takenaka, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 1073 days.

(21) Appl. No.: 11/794,339

(22) PCT Filed: Aug. 11, 2005

(86) PCT No.: PCT/JP2005/015034
§ 371 (c)(1),
(2), (4) Date: Sep. 24, 2007

(87) PCT Pub. No.: WO2006/070505
PCT Pub. Date: Jul. 6, 2006

(65) Prior Publication Data
US 2008/0154165 A1    Jun. 26, 2008

(30) Foreign Application Priority Data
Dec. 28, 2004  (JP) ................................ 2004-382093

(51) Int. Cl.
*A61H 1/02*   (2006.01)
*A61F 5/052*  (2006.01)
*G06F 19/00*  (2011.01)

(52) U.S. Cl. ................. 601/35; 601/5; 601/23; 601/27; 601/33; 601/34; 600/595; 602/19; 602/23; 602/26; 700/245

(58) Field of Classification Search ................ 601/5, 23, 601/27, 33, 34, 35; 600/595; 602/19, 23, 602/26; 700/245
See application file for complete search history.

(56) References Cited

U.S. PATENT DOCUMENTS

| | | | |
|---|---|---|---|
| 6,980,919 B2* | 12/2005 | Ido | 702/150 |
| 7,381,192 B2* | 6/2008 | Brodard et al. | 601/5 |
| 7,785,279 B2* | 8/2010 | Sankai | 601/5 |
| 2004/0158175 A1* | 8/2004 | Ikeuchi et al. | 601/5 |
| 2010/0204627 A1* | 8/2010 | Kazerooni et al. | 602/16 |

FOREIGN PATENT DOCUMENTS

| | | |
|---|---|---|
| CA | 2 559 538 A1 | 9/2005 |
| JP | 5-329186 | 12/1993 |
| JP | 3002320 | 7/1994 |
| JP | 7-112035 | 2/1995 |
| JP | 2000-166997 | 6/2000 |
| JP | 2003-220102 | 5/2003 |

OTHER PUBLICATIONS

Canadian Office Action for application No. 2,587,771 dated Mar. 29, 2010.

* cited by examiner

*Primary Examiner* — Clinton T Ostrup
(74) *Attorney, Agent, or Firm* — Squire Sanders (US) LLP

(57) ABSTRACT

A body weight support device of the present invention is equipped with a body attachment part attached to a user's body, a floor contact part provided contactably on a floor, a leg link part for connecting the body attachment part to the floor contact part through a joint part, an actuator for driving the joint part, and a control unit for controlling a drive of the actuator, wherein the control unit drives the actuator so that the leg link part gives a body weight support force to the user through the body attachment part.

30 Claims, 15 Drawing Sheets

FIG. 1
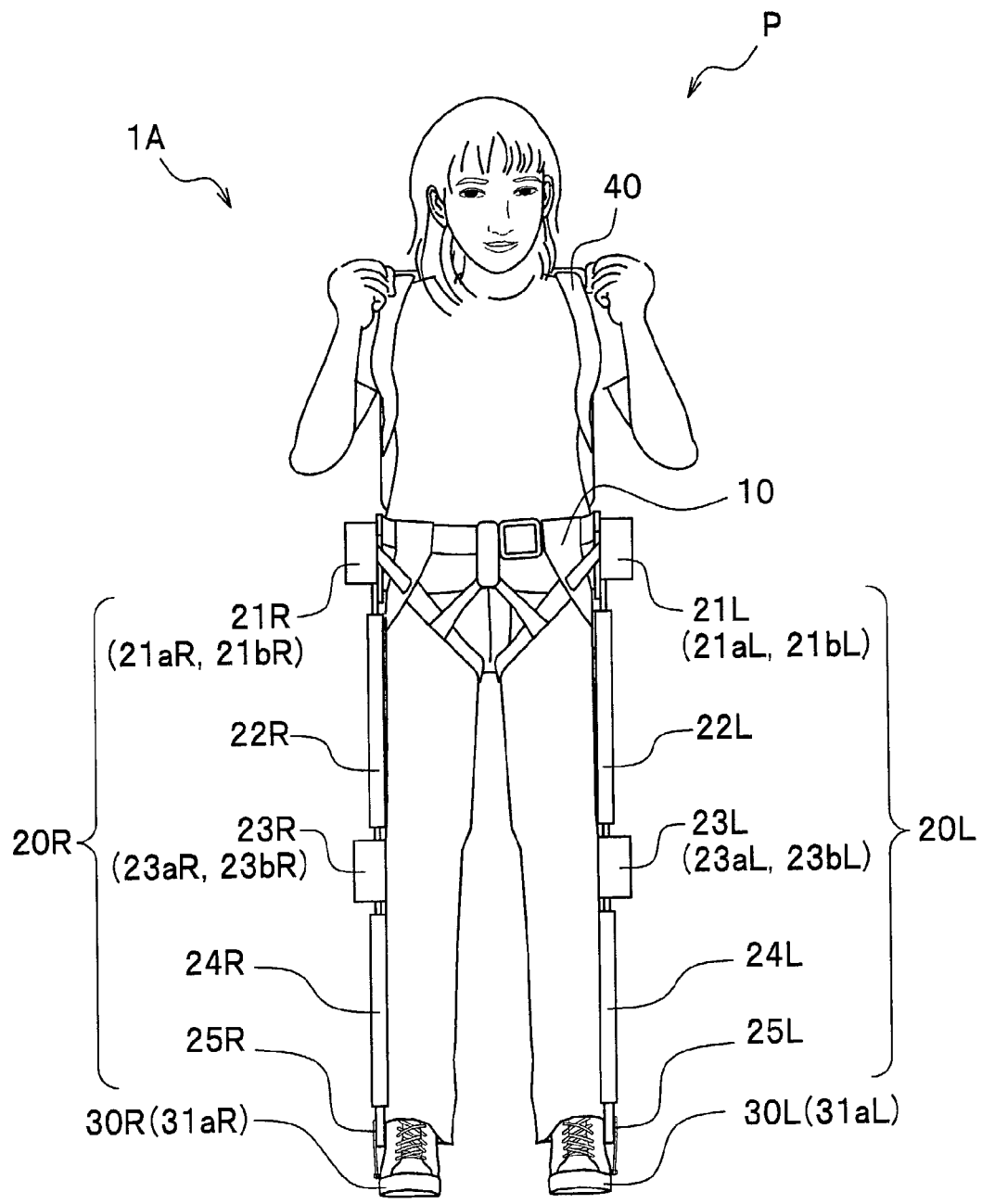
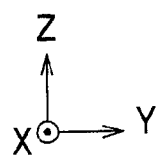

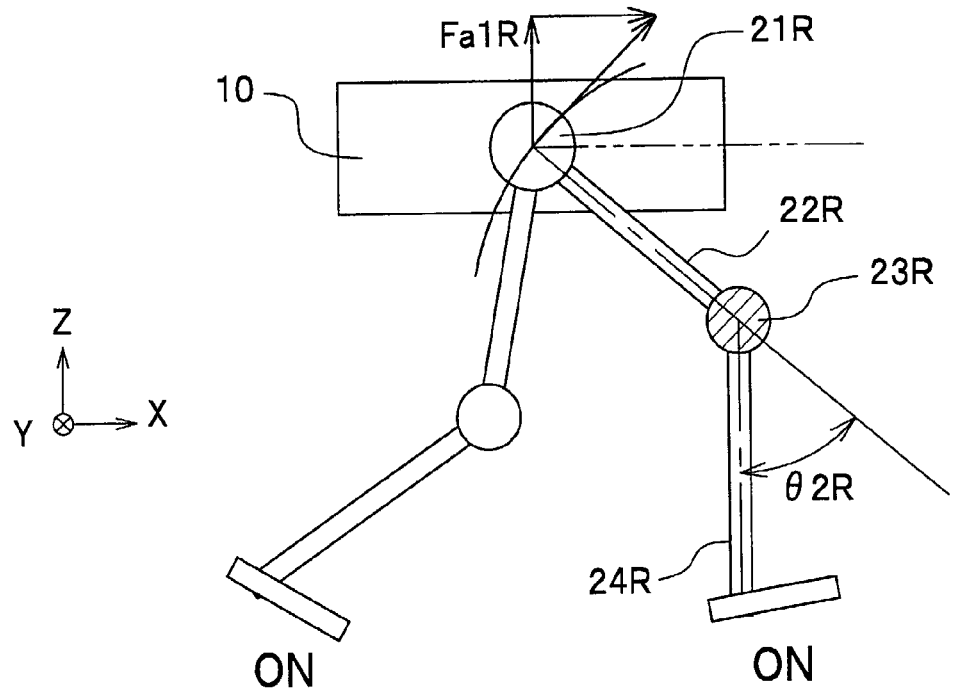
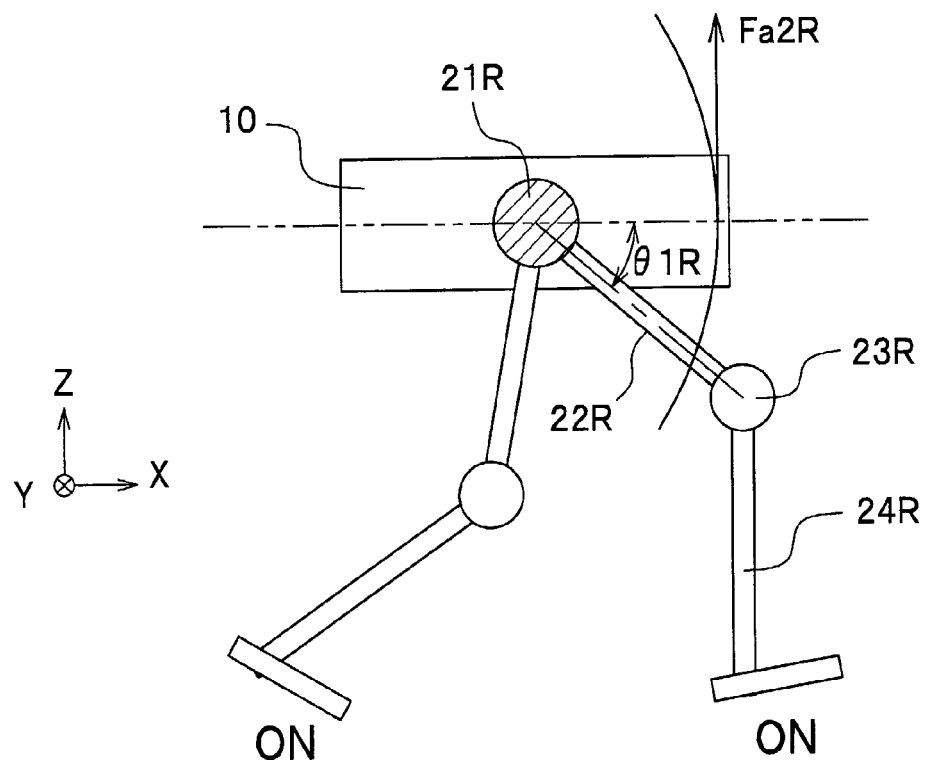

State1

State2

State3

State4

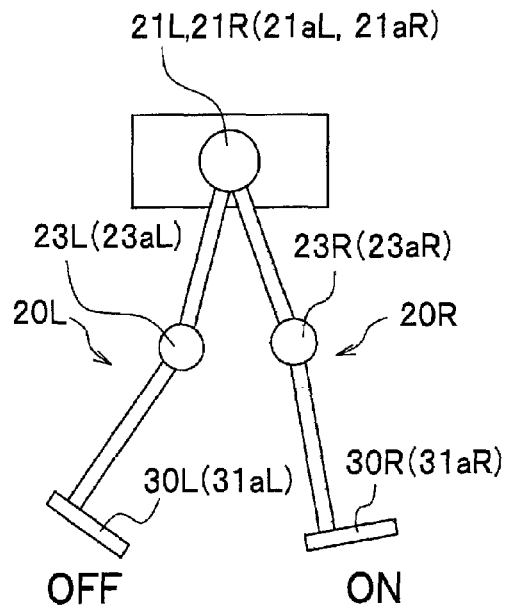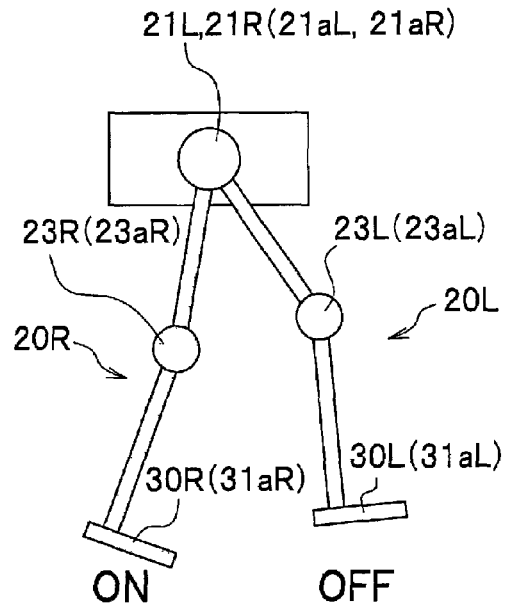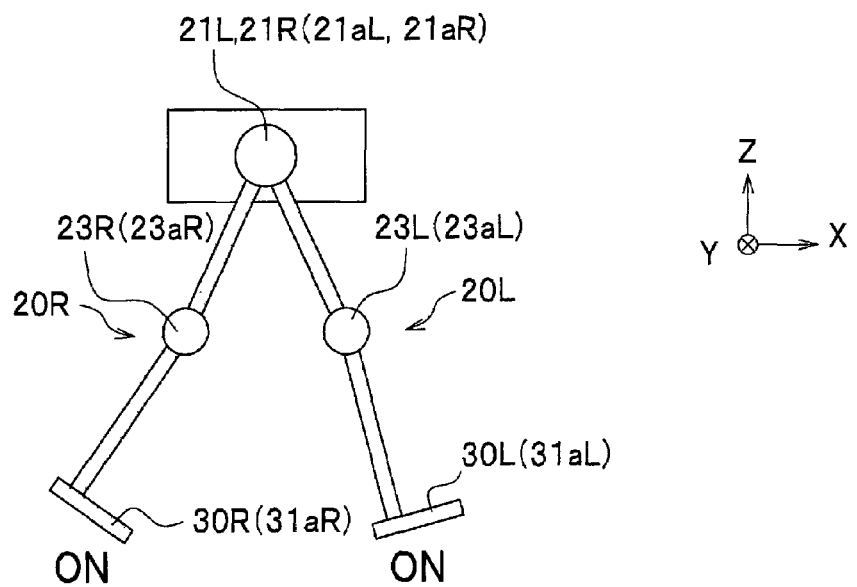

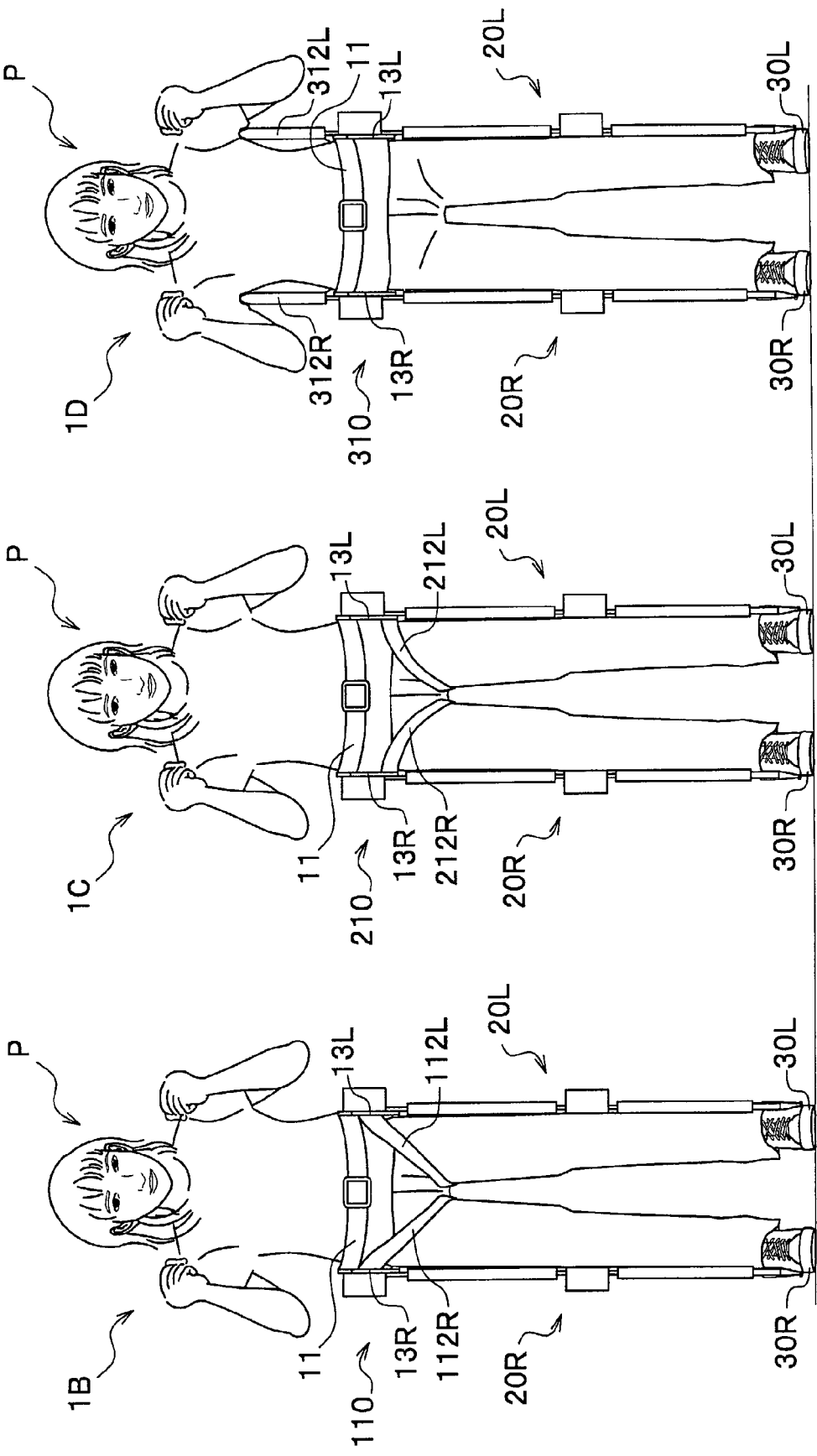

BODY WEIGHT SUPPORT DEVICE AND BODY WEIGHT SUPPORT PROGRAM

TECHNICAL FIELD

The present invention relates to a body weight support device and body weight support program for assisting a weight support by user's own legs.

BACKGROUND ART

Conventionally, it is known a walking assist device giving an assist propulsion for walking for a user. The walking assist device is used for assisting walking of a person who is difficult to walk by herself or himself such as a person whose a muscle force of her or his legs has lessened or whose legs has been injured. In addition, the walking assist device is also expected as such an exercise use and amusement use for aiming an improvement of a muscle force and a walking posture.

A walking aid device described in paragraphs 0034 to 0036 and FIGS. 15 and 16 of Japanese Patent Laid-Open Publication No. Hei. 5-329186 is attached to legs of a user and gives a constant propulsion to the user by rotating joints of a crotch, knees, and ankles with a joint drive device.

Although the walking aid device described in JP Hei. 5-329186 can alleviate a user's fatigue accompanied with her or his movement by giving a propulsion in a walking direction, her or his weight is supported by her or his own legs and a load on the legs due to supporting the weight remains as it is. In addition, because the walking aid device firmly constrains user's whole legs with support members, he or she tends to feel an uncomfortable constraint feeling and an ache. Furthermore, such a configuration of constraining the whole legs with the support members needs to make the members fit each user well according to a body type and a way in walking.

Consequently, it is strongly requested a body weight support device that can alleviate a constraint of user's legs, is lightweight, and can reduce a load on the legs; and a body weight support program thereof.

DISCLOSURE OF THE INVENTION

A first aspect of the present invention is a body weight support device that comprises a body attachment part attached to a body of a user, a floor contact part provided contactably on a floor, a leg link part for connecting the body attachment part to the floor contact part through a joint part including a knee joint part, the leg link part capable of bending at the knee joint part in only one direction when the user wears the body weight support device, an actuator for driving the joint part, and a control unit for controlling driving of the actuator, the control unit driving the actuator to produce rotational power at the knee joint part, so that the leg link part gives a body weight support force to the user through the body attachment part, the body weight support force being a force for partially supporting weight of the user, and the leg link part is provided not to exert the body weight support force directly on upper or lower thighs or knee joints of the user while the user is wearing the body weight support device, and the leg link part is kept bent while the user is wearing the body weight support device.

A second aspect of the present invention is the body weight support device of the first aspect wherein the leg link part comprises the knee joint part, an upper thigh link part and an lower thigh link part, the upper thigh link part being coupled to the body attachment part and to the knee joint part, the lower thigh link part being coupled to the floor contact part and to the knee joint part, and wherein the leg link part bends at the knee joint part only in the same direction as a leg of the user does when the user wears the body weight support device.

A third aspect of the present invention is the body weight support device of the second aspect wherein the actuator comprises a knee joint part actuator for driving the knee joint part, and wherein the leg link part and the knee joint part actuator are provided along the leg of the user.

A fourth aspect of the present invention is the body weight support device of the first aspect wherein the leg link part is provided on the upper or lower thighs or the knee joints of the user in such a way that the leg link part does not fasten the upper or lower thighs or the knee joints of the user while the user is wearing the body weight support device.

A fifth aspect of the present invention is the body weight support device of the first aspect wherein the control unit drives the actuator in such a way that the leg link part is not stretched or does not bend in the opposite direction while the user is wearing the body weight support device.

A sixth aspect of the present invention is the body weight support device of the first aspect further comprising a stopper being provided in the leg link par or the actuator wherein the stopper allows the leg link part not to be stretched or not to bend in the opposite direction while the user is wearing the body weight support device.

A seventh aspect of the present invention is the body weight support device of the first aspect wherein at least part of the leg link part is provided outside the leg of the user.

An eighth aspect of the present invention is the body weight support device of the first aspect wherein at least part of the leg link part is provided inside the leg of the user.

Here, the "body weight support force" means a force for supporting part of a user's weight. Thus it is enabled to reduce a load due to a user's weight on her or his legs. The "weight" is, a weight where the user's weight and that of user's clothes and belongings are added and which the user must support by her or his own legs if he or she does not use the body weight support device of the present invention.

In addition, the joint part may be provide in at least one place of a connection portion of the body attachment part and the leg link part, that of the floor contact part and the leg link part, and an intermediate portion of the leg link part, and it is also considered that the joint part is provided, as one example, coaxially to a joint of the leg of the user.

Thus it is enabled to provide a body weight support device that can alleviate a constraint of user's legs, is lightweight, and can reduce a load on the legs.

When the leg link part and the actuator are positioned along the leg of the user, they easily synchronize the motion of the leg. This makes it possible to transmit the body weight support force.

A ninth aspect of the present invention is the body weight support device of the first aspect that further comprises a floor contact detection mechanism for detecting a user's foot contact with a floor, wherein if the floor contact detection mechanism detects the floor contact, the control unit drives the actuator so that the leg link part gives the body weight support force to the user.

A tenth aspect of the present invention is the body weight support device of the ninth aspect wherein if the floor contact detection mechanism does not detect the floor contact, the control unit terminates driving of the actuator and makes the joint part rotation-free.

Here, the "user's foot contact with a floor" means a state of a floor reaction force being input in a user's foot. In other words, the "user's foot contact with a floor" includes not only a case of a user's foot directly contacting a floor but also a case of a shoe put on by her or him contacting the floor. Thus it is enabled to generate a body weight support force only when necessary.

Thus in accordance with the tenth aspect of the present invention, there is no interruption of a motion of a user's foot not in contact with the floor.

In addition, a twelfth aspect of the present invention is the body weight support device of the tenth aspect, wherein the actuator comprises a crotch joint to part actuator for driving a crotch joint part provided in the leg link part, and wherein if the floor contact detection mechanism does not detect the floor contact, the control unit drives the crotch joint part actuator so as to assist a upper thigh of the user to swing forward.

Moreover, an eleventh aspect of the present invention is a body weight support device comprising a body attachment part attached to a body of a user, a floor contact part provided contactably on a floor, a leg link part for connecting the body attachment part to the floor contact part through a joint part including a knee joint part, the leg link part capable of bending at the knee joint part in only one direction when the user wears the body weight support device, an actuator for driving the joint part, a control unit for controlling driving of the actuator, and the control unit driving the actuator to produce rotational power at the knee joint part, so that the leg link part gives a body weight support force to the user through the body attachment part, the body weight support force being a force for partially supporting weight of the user, the leg link part being provided not to exert the body weight support force directly on upper or lower thighs or knee joints of the user while the user is wearing the body weight support device, a floor contact detection mechanism for detecting a user's foot contact with a floor, wherein if the floor contact detection mechanism detects the floor contact, the control unit drives the actuator so that the leg link part gives the body weight support force to the user, the actuator comprising a crotch joint part actuator for driving a crotch joint part provided in the leg link part, and wherein if the floor contact detection mechanism does not detect the floor contact, the control unit drives the crotch joint part actuator so as to assist an upper thigh of the user to swing forward.

A twelfth aspect of the present invention is a body weight support device comprising a body attachment part attached to a body of a user, a floor contact part so provided contactably on a floor, a leg link part for connecting the body attachment part to the floor contact part through a joint part including a knee joint part, the leg link part capable of bending at the knee joint part in only one direction when the user wears the body weight support device, an actuator for driving the joint part, a control unit for controlling driving of the actuator, the control unit driving the actuator to produce rotational power at the knee joint part, so that the leg link part gives a body weight support force to the user through the body attachment part, the body weight support force being a force for partially supporting weight of the user, the leg link part being provided not to exert the body weight support force directly on upper or lower thighs or knee joints of the user while the user is wearing the body weight support device, a floor contact detection mechanism for detecting a user's foot contact with a floor, wherein if the floor contact detection mechanism detects the floor contact, the control unit drives the actuator so that the leg link part gives the body weight support force to the user, and wherein in the control unit, a predetermined value of a target body weight support force is set, and wherein if the floor contact detection mechanism detects the floor contact, the control unit drives the actuator so that the leg link part gives the target body weight support force to the user, a load detection mechanism for detecting a load of the user on the leg link part through the body attachment part, wherein in the control unit, a lower limit value and upper limit value of the target body weight support force are set, and the control unit drives the actuator so that the body weight support force by the leg link part falls between the lower and upper limit values of the target body weight support force, based on the load detected by the load detection mechanism.

Thus in accordance with the twelfth aspect of the present invention, it is enabled to assist a motion of a user's foot not in contact with the floor.

In addition, a thirteenth aspect of the present invention is the body weight to support device of the twelfth aspect, wherein in the control unit, the target body weight support force is set to have a predetermined ratio of a weight of the user.

Thus in accordance with the thirteenth aspect of the present invention, it is enabled to give a predetermined body weight support force even if a user's posture changes.

In addition, a fourteenth aspect of the present invention is the body weight support device of the first, eleventh or twelfth aspect that further comprises a load detection mechanism for detecting a load of the user on the leg link part through the body attachment part wherein the control unit drives the actuator, based on the load detected by the load detection mechanism.

If a load detected by the load detection mechanism is smaller than the lower limit value of the target body weight support force, the control unit drives the actuator so as to enlarge the load. In addition, if the load detected by the load detection mechanism is larger than the upper limit value of the target body weight support force, the control unit drives the actuator so as to lessen the load.

Thus it is prevented for the body weight support force to become too large or too small, and it is enabled to control the drive of the actuator so as to give a correct range of a body weight support force.

In addition, a fifteenth aspect of the present invention is the body weight support device of the first, eleventh or twelfth aspect, wherein a portion where the body weight support force is given to the user through the leg link part and a portion where a load of the user in the body attachment part is loaded are positioned within substantially the same vertical plane.

Here, the "vertical plane" means a plane vertical to a floor or parallel to a gravity direction. Thus in accordance with the tenth aspect of the present invention the body weight support device can prevent an unnecessary moment in a pitch direction (around a Y-axis) from being generated in a user.

In addition, a sixteenth aspect of the present invention is the body weight support device of to the first, eleventh or twelfth aspect that further comprises a leg link part behavior detection mechanism for detecting a behavior of the leg link part, wherein the control unit drives the actuator, based on the behavior detected by the leg link part behavior detection mechanism.

A load detected by the load detection mechanism corresponds to a body weight support force by the leg link part. Thus in accordance with the eighth aspect of the present invention, feedback control using a current body weight support force is enabled.

In addition, a seventeenth aspect of the present invention is the body weight support device of the first, eleventh or twelfth aspect, wherein the floor contact part is a foot attachment part attached to a foot of the user.

In addition, an eighteenth aspect of the present invention is the body weight support device of the first aspect, further comprising a leg link part behavior detection mechanism for detecting a behavior of the leg link part, wherein the control unit predicts that the contact between the floor and the leg of the user is to be released based on the detection result of the leg link part behavior detection mechanism, and the control unit decreases the body weight support force produced by the leg link part, before the leg of the user comes off the floor.

As an example of the leg link part behavior detection mechanism can be cited a rotary encoder for detecting a rotation angle of the actuator. Thus in accordance with the eleventh aspect of the present invention the body weight support device can control a drive amount of the actuator according to a state of the leg link part, and a body weight support is enabled that does not give a bad influence on a user's posture.

In addition, a nineteenth aspect of the present invention is the body weight support device of the eighteenth aspect, further comprising a floor contact detection mechanism for detecting contact between a floor and the leg of the user, wherein the control unit predicts that the contact between the floor and the leg of the user is to be released based on the detection results of the floor contact detection mechanism and the leg link part behavior detection mechanism, and the control unit decreases the body weight support force produced by the leg link part, before the leg of the user comes off the floor.

Thus in accordance with the nineteenth aspect of the present invention the body weight support device can make the floor contact part easily comes in contact with a floor.

In addition, a twentieth aspect of the present invention is a body weight support program comprising the function of making a computer as an output instruction unit drive an actuator so that a leg link part gives a body weight support force to a user through a body attachment part, in order to control a body weight support device that comprises said body attachment part attached to a body of said user, a floor contact part provided contactably on a floor, a leg link part for connecting said body attachment part to said floor contact part through a joint part including a knee joint part, and said actuator for driving said joint part to produce the body weight support force, wherein said control unit drives said actuator to produce rotational power at the knee joint part, so that said leg link part gives the body weight support force to said user through said body attachment part, the body weight support force being a force for partially supporting weight of the user, wherein the leg link part is provided not to exert the body weight support force directly on the upper or lower thighs or crotch joints of the user while the user is wearing said body weight support device, wherein the output instruction unit drives the leg link part so as to bend at the knee joint, part in only one direction, when the user wears the body weight support device, and wherein the output instruction unit drives the actuator in such a way that the leg link part is not stretched, while the user is wearing the body weight support device.

A twenty first aspect of the present invention is the body weight support program of the twentieth aspect further comprising the function of making said computer as a floor contact determination unit determine whether or not a leg of said user has come in contact with a floor, based on a detection result of a floor contact detection mechanism, wherein said body weight support device further comprises, said floor contact detection mechanism for detecting contact between the leg of said user and the floor, and wherein if said floor contact determination unit determines that the leg of said user has come in contact with the floor, said output instruction unit drives said actuator so as to give the body weight support force to said user.

In addition, a twenty second aspect of the present invention is the body weight support program of the twenty first aspect, wherein if said floor contact determination unit determines that a leg of said user is not contact with a floor, said output instruction unit terminates driving of said actuator and makes said joint part rotation-free.

In addition, a twenty third aspect of the present invention is the body weight support program comprising the function of making a computer as an output instruction unit drive an actuator so that a leg link part gives a body weight support force to a user through a body attachment part, in order to control a body weight support device that comprises said body attachment part attached to a body of said user, a floor contact part provided contactably on a floor, a leg link part for connecting said body attachment part to said floor contact part through a joint part including a knee joint part, and said actuator for driving said joint part to produce the body weight support force, wherein said control unit drives said actuator to produce rotational power at the knee joint part, so that said leg link part gives the body weight support force to said user through said body attachment part, the body weight support force being a force for partially supporting weight of the user, wherein the leg link part is provided not to exert the body weight support force directly on the upper or lower thighs or crotch joints of the user while the user is wearing said body weight support device, and wherein the output instruction unit drives the leg link part so as to bend at the knee joint part in only one direction, when the user wears the body weight support device, the body weight support program further comprising the function of making said computer as a floor contact determination unit determine whether or not a leg of said user has come in contact with a floor, based on a detection result of a floor contact detection mechanism, wherein said body weight support device further comprises said floor contact detection mechanism for detecting contact between the leg of said user and the floor, and wherein if said floor contact determination unit determines that the leg of said user has come in contact with the floor, said output instruction unit drives said actuator so as to give the body weight support force to said user, and wherein said body weight support device further comprises a crotch joint part actuator for driving, as said actuator, a crotch joint part provided in said leg link part, and wherein if said floor contact determination unit determines that a leg of said user is not contact with a floor, said output instruction unit drives said crotch joint part actuator so as to assist an upper thigh of said user to swing forward.

In addition, a twenty fourth aspect of the present invention is the body weight support program comprising the function of making a computer as an output instruction unit drive an actuator so that a leg link part gives a body weight support force to a user through a body attachment part, in order to control a body weight support device that comprises said body attachment part attached to a body of said user, a floor contact part provided contactably on a floor, a leg link part for connecting said body attachment part to said floor contact part through a joint part including a knee joint part, and said actuator for driving said joint part to produce the body weight support force, wherein said control unit drives said actuator to produce rotational power at the knee joint part, so that said leg link part gives the body weight support force to said user through said body attachment part, the body weight support force being a force for partially supporting weight of the user, wherein the leg link part is provided not to exert the body weight support force directly on the upper or lower crotch joints of the user while the user is wearing said body weight support device, and wherein the output instruction unit drives the leg link part so as to bend at the knee joint part in only one direction, when the user wears the body weight support device, the body weight support program further comprising the functions of making said computer as a floor contact determination unit determine whether or not a leg of said user has come in contact with a floor, based on a detection result of a floor contact detection mechanism, wherein said body weight support device further comprises said floor contact detection mechanism for detecting contact between the leg of said user and the floor, and wherein if said floor contact determination unit determines that the leg of said user has come in contact with the floor, said output instruction unit drives said actuator so as to give the body weight support force to said user, and making said computer as a target assist force memory unit memorize a predetermined value of the target body weight support force, wherein if said floor contact determination unit determines that a leg of said user has come in contact with a floor, said output instruction unit drives said actuator so that said leg link part gives said target body weight support force to said user, wherein said body weight support device further comprises a load detection mechanism for detecting a load of said user on said leg link part through said body attachment part, wherein the load detection mechanism presets a lower value and an upper value of the target body weight support force, said target body weight support force has a lower limit value and upper limit value thereof, and said output instruction unit drives said actuator so that the body weight support force by said leg link part falls between said lower and upper limit values of said target body weight support force, based on the load detected by said load detection mechanism.

In addition, a twenty fifth aspect of the present invention is the body weight support program of the twenty fourth aspect, further comprising the function of making said computer as a weight memory unit memorize a weight of said user and as a target assist force calculation unit calculate a target body weight support force having a predetermined ratio of the weight of said user, based on said weight.

In addition, a twenty sixth aspect of the present invention is the body weight support program of the twentieth, twenty third or twenty fourth aspect, wherein said body weight support device further comprises a load detection mechanism for detecting a load of said user on said leg link part through said body attachment part, and wherein said output instruction unit drives said actuator, based on the load detected by said load detection mechanism.

In addition, a twenty seventh aspect of the present invention is the body weight support program of the twentieth, twenty third or twenty fourth aspect, wherein said body weight support device further comprises a leg link part behavior detection mechanism for detecting a behavior of said leg link part, and wherein said output instruction unit drives said actuator, based on the behavior detected by said leg link part behavior detection mechanism.

In addition, a twenty eighth aspect of the present invention is the body weight support program of the twentieth aspect, wherein the body weight support device further comprises a leg link part behavior detection mechanism for detecting a behavior of the leg link part, and wherein the output instruction unit predicts that the contact between the floor and the leg of the user is to be released based on the detection result of the leg link part behavior detection mechanism, and the output instruction unit decreases the body weight support force produced by the leg link part, before the leg of the user comes off the floor.

In addition, a twenty ninth aspect of the present invention is the body weight support program of the twentieth aspect, wherein the body weight support device further comprises a floor contact detection mechanism for detecting contact between a floor and the leg of the user, wherein the output instruction unit predicts that the contact between the floor and the leg of the user is to be released based on the detection result of the floor contact detection mechanism, and the output instruction unit decreases the body weight support force produced by the leg link part, before the leg of the user comes of the floor.

BRIEF DESCRIPTION OF DRAWINGS

FIG. 1 is a front view showing a body weight support device related to an embodiment of the present invention.

FIG. 5A is a front view; FIG. 5B is a rear view; and FIG. 5C is a side view.

FIG. 6A is a rear view; FIG. 6B is a side view; and FIG. 6C is a plan view.

FIG. 8A is a schematic drawing showing a state of a torque being sufficiently generated; and FIG. 8B is a schematic drawing showing such a state of torque being insufficient and a user being becoming a state of losing her or his balance.

FIG. 9 is a drawing illustrating a relationship between a generation torque and a body weight support force, between the generation torque of a knee joint part actuator and the body weight support force.

FIG. 10 is a drawing illustrating a relationship between a generation torque and a body weight support force, between the generation torque of a crotch joint part actuator and the body weight support force.

FIGS. 14A, 14B, and 14C are drawings showing a state transition of the right leg link part in the user's walking.

FIGS. 15A, 15B, and 15C are drawings showing variation examples of a body attachment part.

BEST MODE(S) FOR CARRYING OUT THE INVENTION

A principle of the present invention exists in a point that a floor contact side of a body weight support device generates a predetermined support force in a reverse direction to a gravity direction according to a user's walking, gives the support force to the user through a portion contacting the user, and thereby alleviates a weight support amount by the user's own legs.

The weight support force generated by the body weight support device of the present invention is given to, for example, such a crotch, upper thighs, a waist, armpits, and a jaw of a user.

Here will be described an embodiment of the present invention, referring to drawings as needed. A same symbol will be appended to a similar portion, and a duplicated description will be omitted. Meanwhile, with respect to an expression concerning a position, a direction, and the like, an X-axis is assumed to be in a user's front/back direction, a Y-axis in a user's left/right direction, and a Z-axis in a user's up/down direction; and a description is made with making it a standard a state of a user's taking a standup posture. In addition, with respect to members provided to become a pair in left/right such as leg link parts, in a case of distinguishing them, an L (left) or an R (right) is appended to an end of a symbol; and in a case of not distinguishing them, a description is made without appending the L or the R.

Figure 2:
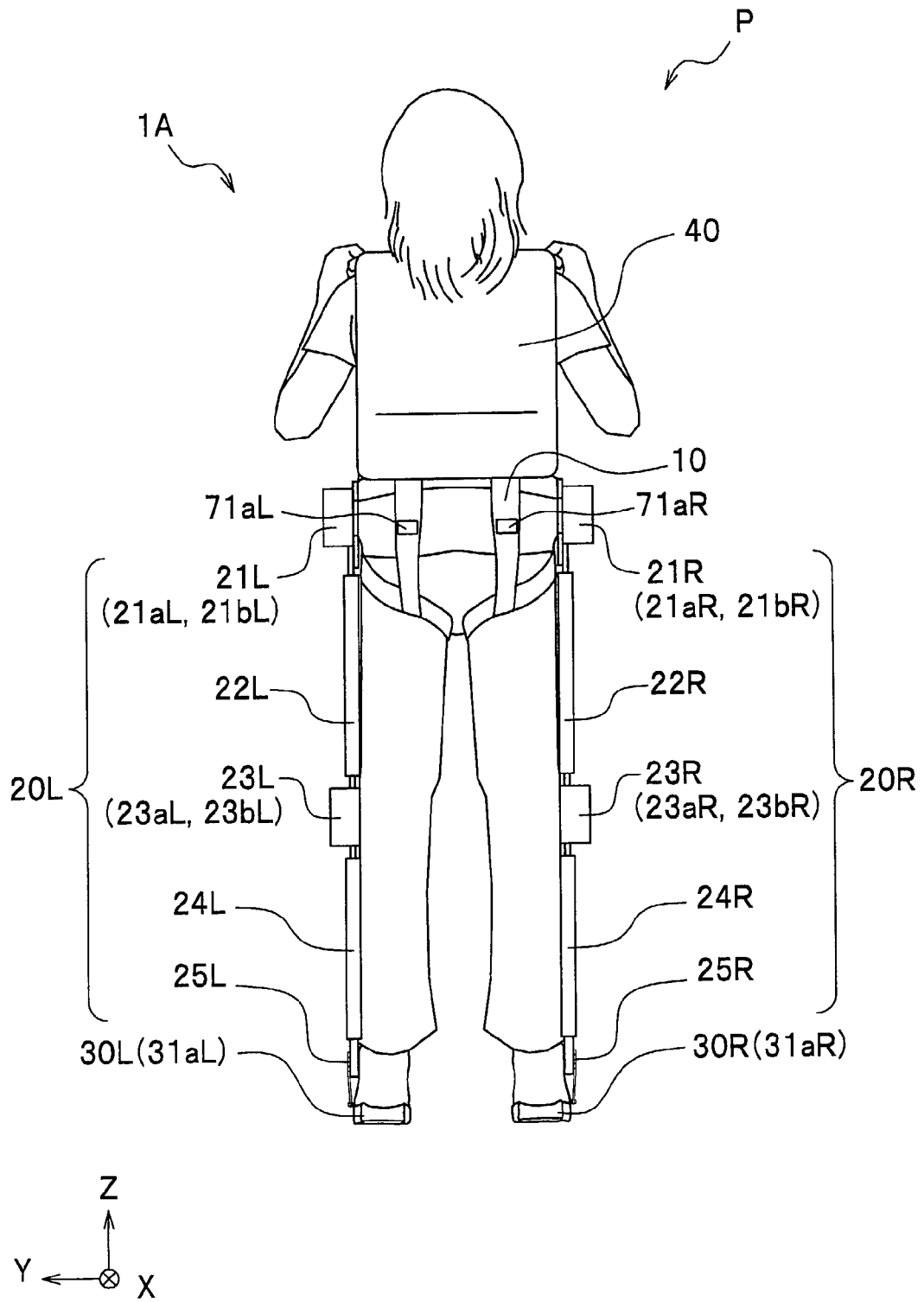
FIG. 2 is a rear view of the body weight support device.
Figure 3:
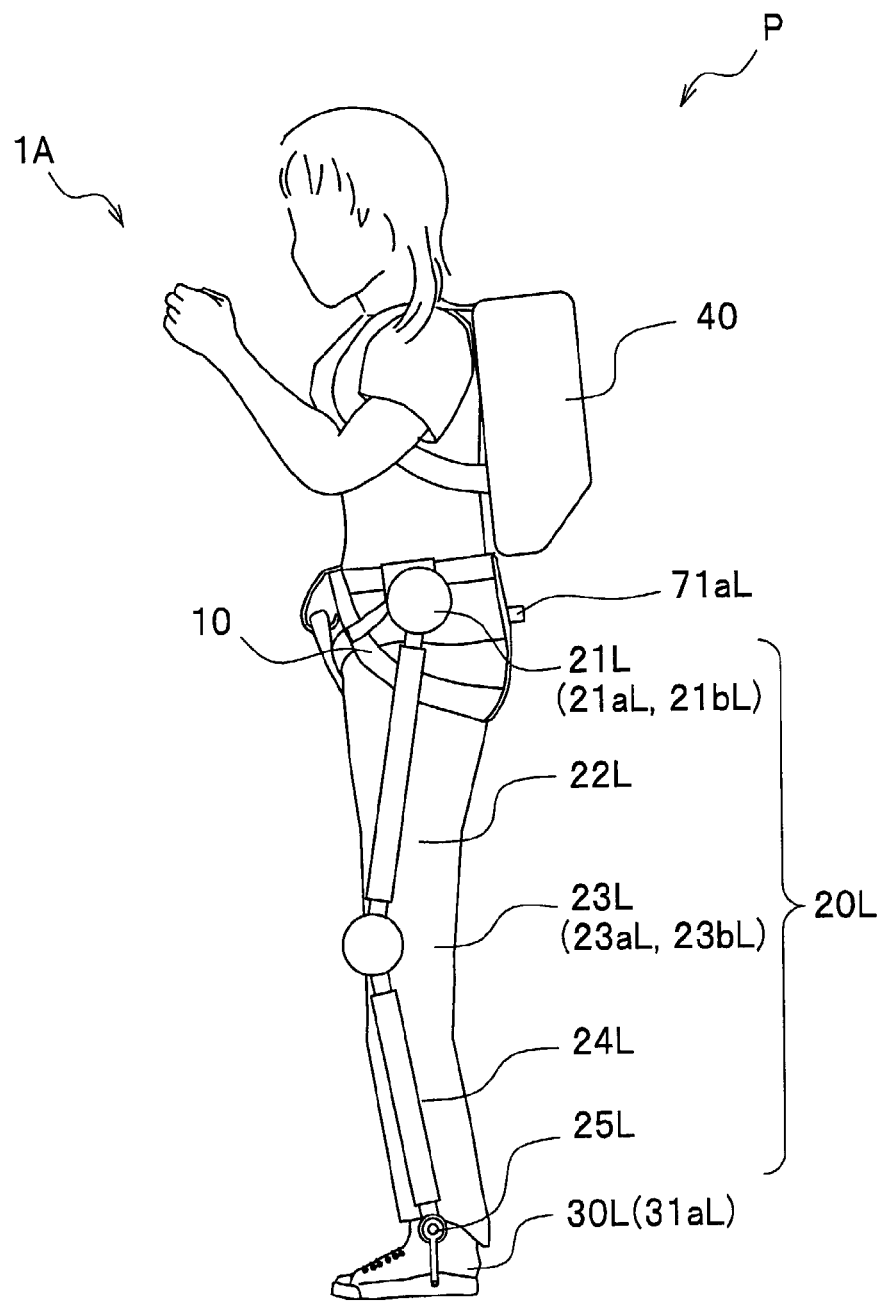
FIG. 3 is a side view of the body weight support device.
Figure 4:
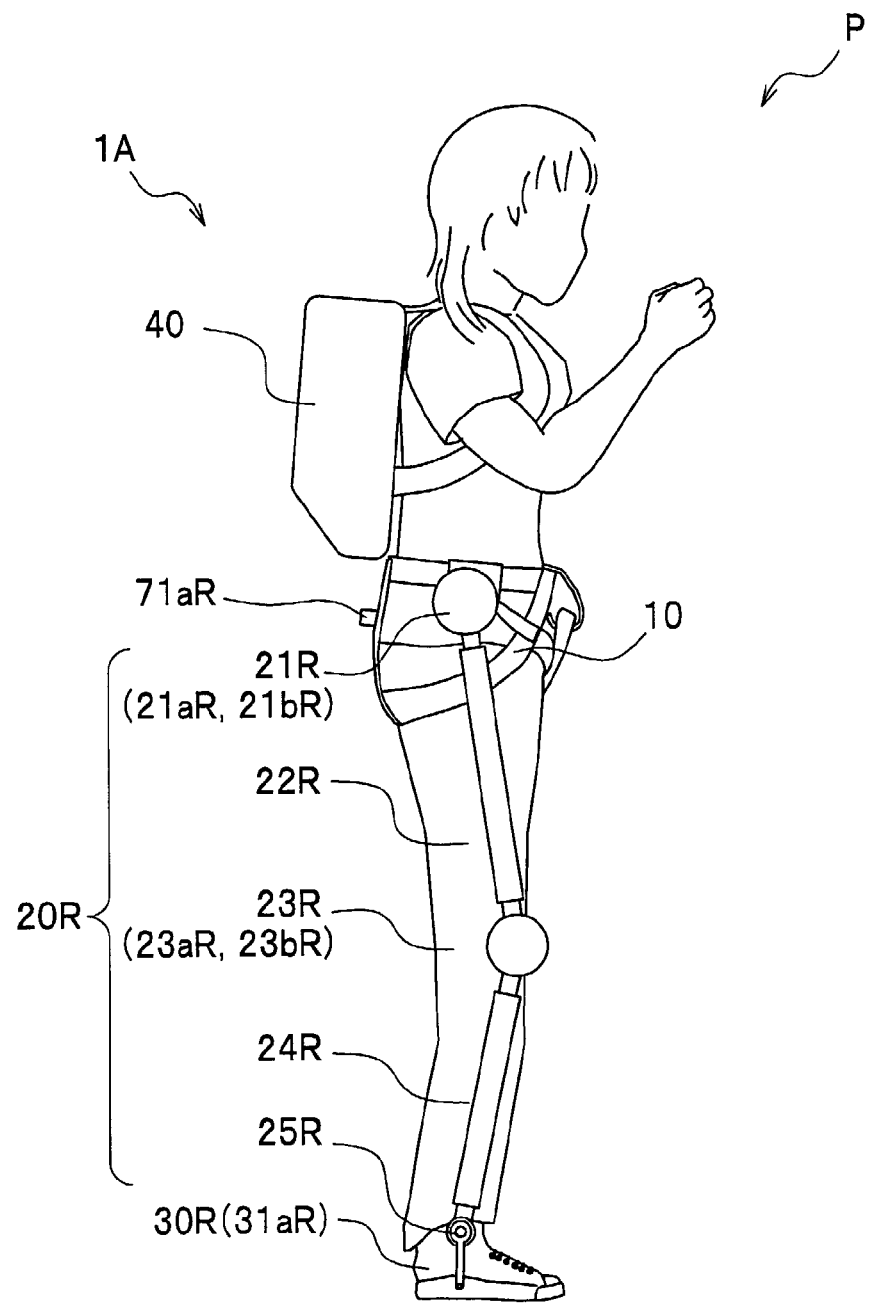
FIG. 4 is a side view of the body weight support device.
Figure 5A:
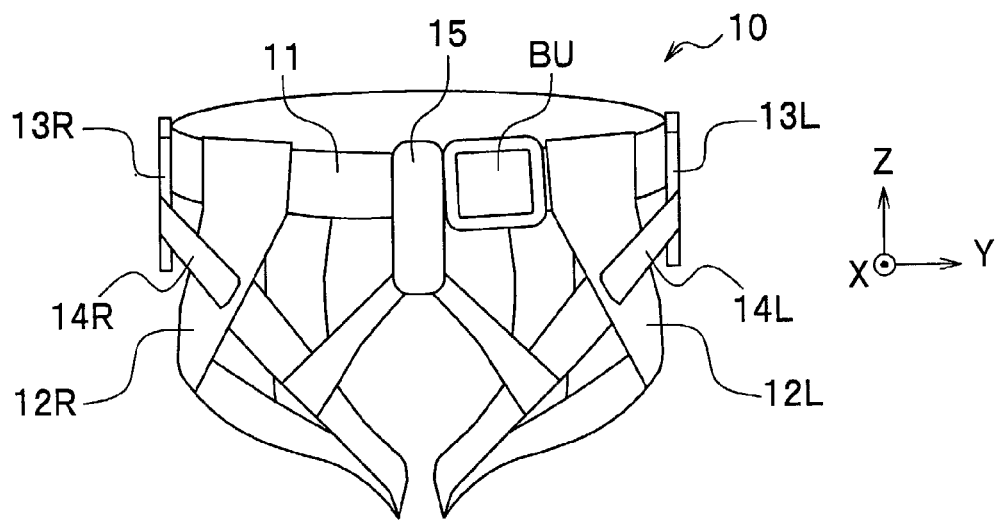
FIGS. 5A to 5C are drawings showing a body attachment part.
Figure 5B:
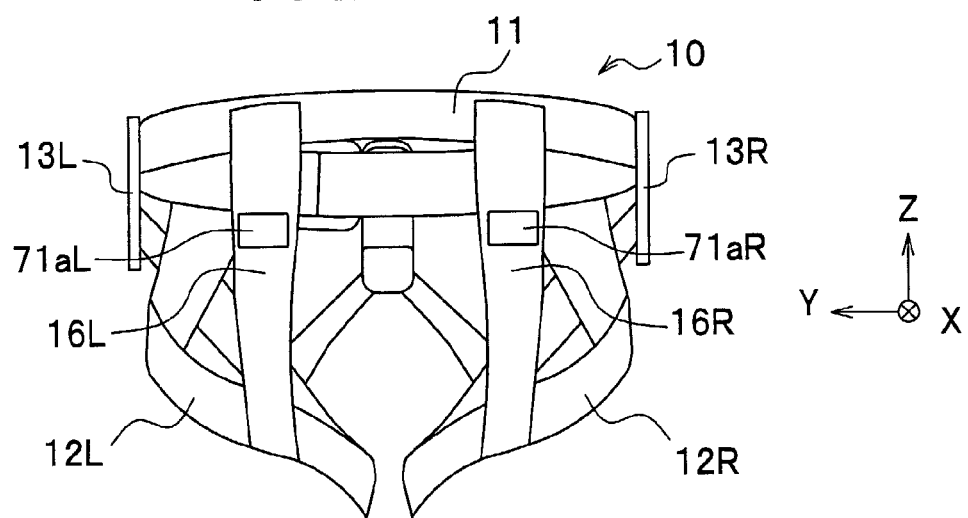
Figure 5C:
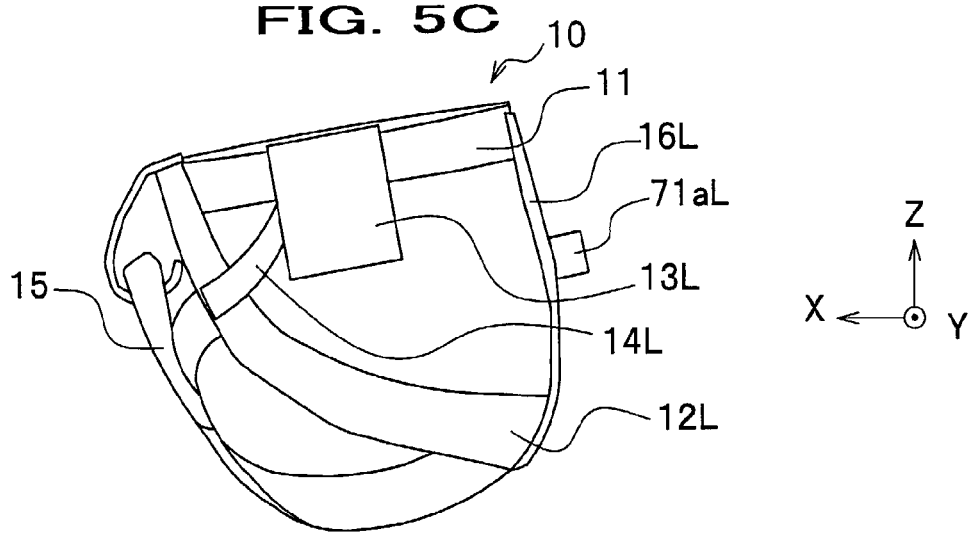
Figure 6B:
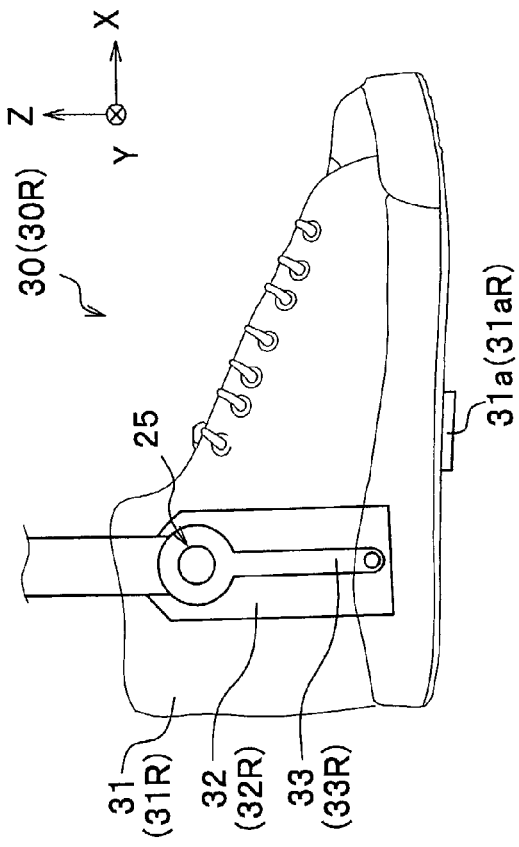
FIGS. 6A to 6C are drawings showing a foot attachment part.
Figure 6C:
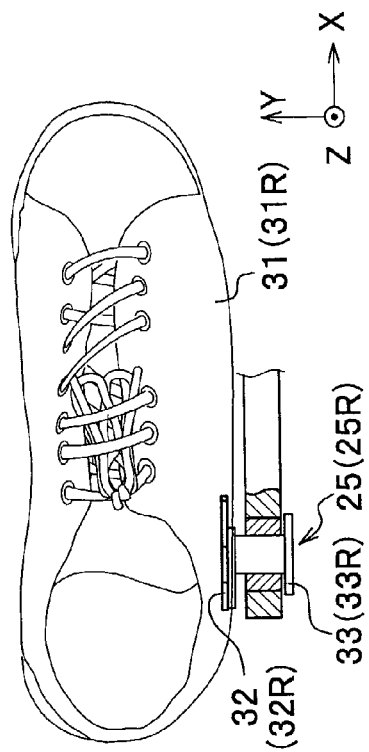
Figure 6A:
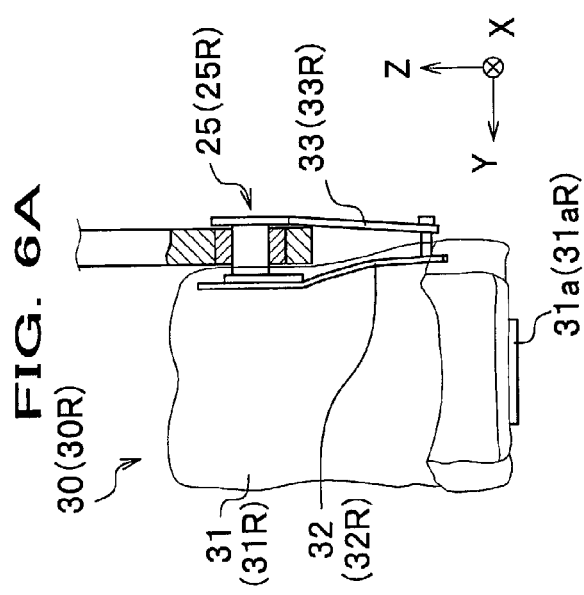

Firstly, an embodiment of a body weight support device of the present invention will be described. FIGS. 1 to 4 are drawings showing appearances of the body weight support device related to the embodiment of the present invention; FIG. 1 is a front view; FIG. 2 is a rear view; FIG. 3 is a side view; and FIG. 4 is a side view. FIGS. 5A to 5C are drawings showing a body attachment part; FIG. 5A is a front view; FIG. 5B is a rear view; and FIG. 5C is a side view. FIGS. 6A to 6C are drawings showing a foot attachment part; FIG. 6A is a rear view; FIG. 6B is a side view; and FIG. 6C is a plan view. In FIGS. 1 to 4 are shown states of a user P who has attached (put on) a body weight support device 1A. Meanwhile, for convenience' sake of a description, in these drawings wiring for connecting each actuator, each sensor, a control unit, a battery, and the like is omitted.

As shown in FIGS. 1 to 4, the body weight support device 1A related to the embodiment of the present invention comprises a body attachment part 10, leg link parts 20 (left leg link part 20L, right leg link part 20R), foot attachment parts 30 (left foot attachment part 30L, right foot attachment part 30R), and a backpack 40.

In addition, an actuator of the body weight support device 1A comprises crotch joint part actuators 21a (left crotch joint part actuator 21aL, right crotch joint part actuator 21aR) and knee joint part actuators 23a (left knee joint part actuator 23aL, right knee joint part actuator 23aR).

[Body Attachment Part]

As shown in FIGS. 1 to 4, the body attachment part 10 is a part attached to a trunk of the user P. As shown in FIGS. 5A to 5C, the body attachment part 10 comprises a waist belt part 11, upper thigh belt parts 12 (left upper thigh belt part 12L, right upper thigh belt part 12R), actuator attachment parts 13 (left actuator attachment part 13L, right actuator attachment part 13R), reinforcement members 14 (left reinforcement member 14L, right reinforcement member 14R), and loosing prevention belt parts 15 and 16 (left loosing prevention belt part 16L, right loosing prevention belt part 16R).

The waist belt part 11 is a girdle-form cloth member attached around the waist of the user P, and it is enabled to set a stop position by a buckle BU and to adjust a length in attachment thereof.

The upper thigh belt parts 12 (12L, 12R) are girdle-form cloth members attached around the upper thighs of the user P and upper ends thereof are fixed to the waist belt part 11.

The actuator attachment parts 13 (13L, 13R) are resin members for fitting the crotch joint part actuators 21a (21aL, 21aR) (see FIG. 1) described later and are provided at left/right ends of the waist belt part 11, respectively.

The reinforcement members 14 (14L, 14R) are resin members for connecting the upper thigh belt parts 12 (12L, 12R) and the actuator attachment parts 13 (13L, 13R), and reinforces the actuator attachment parts 13 (13L, 13R) not to twist due to a torque counteraction of the crotch joint part actuators 21a (21aL, 21aR).

The loosing prevention belt part 15 is a cloth member for connecting the waist belt part 11 and the upper thigh belt parts 12 (12L, 12R) at the front side of the user P, and prevents the upper thigh belt parts 12 (12L, 12R) from loosening downward.

The loosing prevention belt parts 16 (16L, 16R) are cloth members for connecting the waist belt part 11 and the upper thigh belt parts 12 (12L, 12R) at the back side of the user P, and prevents the upper thigh belt parts 12 (12L, 12R) from loosening downward.

Meanwhile, the waist belt part 11 and the upper thigh belt parts 12 (12L, 12R) may also be made of resin. In addition, the actuator attachment parts 13 (13L, 13R) and the reinforcement members 14 (14L, 14R) may also be made of metal. Furthermore, the loosing prevention belt parts 15 and 16 (16L, 16R) may also be made of metal or resin.

In addition, in the loosing prevention belt parts 16 (16L, 16R) are provided load sensors 71a (71aL, 71aR).

The load sensors 71a (71aL, 71aR) detect a load of the user P on the leg link parts 20 (20L, 20R) through the body attachment part 10 and are one example of the "load detection mechanism" in the "DISCLOSURE OF THE INVENTION." Because when the body weight support device 1A supports part of a weight of the user P, the waist belt part 11 is supported by the leg link parts 20 (20L, 20R) and the foot attachment parts 30 (30L, 30R), and on the other hand, the part of the weight of the user P is loaded on the upper thigh belt parts 12 (12L, 12R), a tension in the Z axis direction by the waist belt part 11 and the upper thigh belt parts 12 (12L, 12R) is generated at the loosing prevention belt parts 16 (16L, 16R). The load sensors 71a (71aL, 71aR) detect the tension, and thereby detect the weight of the user P loaded on the leg link parts 20.

As the load sensors 71a (71aL, 71aR), a sensor using a load cell, a strain gauge, a piezoelectric element, and the like is suitable. Meanwhile, although in the embodiment the load sensors 71a (71aL, 71aR) for a one-axis (Z axis) detection are used, they may also be designed to more accurately detect the weight of the user P loaded on the leg link parts 20, using a load sensor that can detect more than one axis. In addition, the load sensors 71a may also be attached to the loosening prevention belt part 15 at the front side; and fitting the load sensors 71a under the crotch of the user P, they may detect a pushing pressure by the user P.

[Leg Link Parts 20]

The leg link parts 20 (20L, 20R) connect the body attachment part 10 and the foot attachment parts 30 (30L, 30R) through a plurality of joint parts, and are provided along outside of legs of the user P.

The leg link parts 20 (20L, 20R) comprise crotch joint parts 21 (left crotch joint part 21L, right crotch joint part 21R), upper thigh link parts 22 (left upper thigh link part 22L, right upper thigh link part 22R), knee joint parts 23 (left knee joint part 23L, right knee joint part 23R), lower thigh link parts 24 (left lower thigh link part 24L, right lower thigh link part 24R), and ankle joint parts 25 (left ankle joint part 25L, right ankle joint part 25R), respectively.

The crotch joint parts 21 (21L, 21R) are positioned outside crotch joints of the user P, respectively, and are nodes for rotatably connecting the waist belt part 11 and the upper thigh link parts 22 (22L, 22R) around the Y-axis.

The crotch joint parts 21 (21L, 21R) comprise the crotch joint part actuators 21a (left crotch joint part actuator 21aL, right crotch joint part actuator 21aR) and crotch joint part encoders 21b (left crotch joint part encoder 21bL, right crotch joint part encoder 21bR), respectively.

The crotch joint part actuators 21a (21aL, 21aR) comprise electric motors and reducers, respectively, bases of the actuators 21a (21aL, 21aR) are fixed to left/right parts of the actuator attachment part 13, and output shafts of the actuators 21a (21aL, 21aR) are fixed to upper ends of the upper thigh link parts 22 (22L, 22R). The output shafts of the crotch joint part actuators 21a (21aL, 21aR) rotate around the Y-axis, and thereby the upper thigh link parts 22 (22L, 22R) rotate around the Y-axis, respectively, making the crotch joint part actuators 21a (21aL, 21aR) axes for the waist belt part 11. Accordingly, the crotch joint part actuators 21a (21aL, 21aR) can generate torques between the waist belt part 11 and the upper thigh link parts 22 (22L, 22R). In a state of the crotch joint part actuators 21a (21aL, 21aR) not generating the torques, the crotch joint parts 21 (21L, 21R) become very small in rotation resistance thereof, result in becoming a rotation-free state, and thus do not cause a trouble in swinging forward a leg of the user P. Meanwhile, an attachment relationship of the crotch joint part actuators 21a (21aL, 21aR) is not limited to the above one.

The crotch joint part encoders (rotary encoders) 21b (21bL, 21bR) are one example of the "leg link part behavior detection mechanism" in the "DISCLOSURE OF THE INVENTION," and as data concerning a behavior of the leg link parts 20 (20L, 20R), detect a rotation angle of the crotch joint part actuators 21a (21aL, 21aR). The rotation angle detected is output to a control unit 50.

The upper thigh link parts 22 (22L, 22R) are links extending along outside of upper thighs of the user P. Upper ends of the upper thigh link parts 22 (22L, 22R) are connected to the crotch joint parts 21 (21L, 21R), respectively. In addition, lower ends of the upper thigh link parts 22 (22L, 22R) are connected to the knee joint parts 23 (23L, 23R), respectively.

The knee joint parts 23 (23L, 23R) are positioned outside knee joints of the user P and are nodes for rotatably connecting the upper thigh link parts 22 (22L, 22R) and the lower thigh link parts 24 (24L, 24R) around the Y-axis. The knee joint parts 23 (23L, 23R) comprise the knee joint part actuators 23a (23aL, 23aR) and knee joint part encoders 23b (left knee joint part encoder 23bL, right knee joint part encoder 23bR).

The knee joint part actuators 23a (23aL, 23aR) comprise electric motors and reducers, respectively, bases of the actuators 23a (23aL, 23aR) are fixed to lower ends of the upper thigh link parts 22 (22L, 22R), and output shafts of the actuators 23a (23aL, 23aR) are fixed to upper ends of the lower thigh link parts 24 (24L, 24R). The output shafts of the knee joint part actuators 23a (23aL, 23aR) rotate around the Y-axis, and thereby the lower thigh link parts 24 (24L, 24R) rotate around the Y-axis, making the knee joint parts 23 (23aL, 23aR) axes for the upper thigh link parts 22 (22L, 22R). Accordingly, the knee joint part actuators 23a (23aL, 23aR) can generate torques between the upper thigh link parts 22 (22L, 22R) and the lower thigh link parts 24 (24L, 24R). In a state of the knee joint part actuators 23a (23aL, 23aR) not generating the torques, the knee joint parts 23 (23aL, 23aR) become very small in rotation resistance thereof, result in becoming a rotation-free state, and thus do not cause a trouble in swinging forward a leg of the user P. Meanwhile, the attachment relationship of the knee joint part actuators 23a (23aL, 23aR) is not limited to the above one.

The knee joint part encoders (rotary encoders) 23b (23bL, 23bR) are one example of the "knee link part behavior detection mechanism" in the "DISCLOSURE OF THE INVENTION," and as data concerning the behavior of the leg link parts 20 (20L, 20R), detect a rotation angle of the knee joint part actuators 23a (23aL, 23aR). The rotation angle detected is output to the control unit 50.

The lower thigh link parts 24 (24L, 24R) are links extending along outside of lower thighs of the user P. Upper ends of the lower thigh link parts 24 (24L, 24R) are connected to the knee joint parts 23 (23L, 23R), respectively. In addition, lower ends of the lower thigh link parts 24 (24L, 24R) are connected to the ankle joint parts 25 (25L, 25R), respectively.

The ankle joint parts 25 (25L, 25R) are nodes for rotatably connecting the lower thigh link parts 24 (24L, 24R) and the foot attachment parts 30 (30L, 30R) around the Y-axis. The ankle joint parts 25 (25L, 25R) move, following an operation of ankle joints of the user P, so as not to interrupt her or his walking motion.

[Foot Attachment Parts]

As shown in FIGS. 1 to 4, the foot attachment parts 30 (30L, 30R) are parts attached to feet of the user P. As shown in FIGS. 6A, 6B, and 6C, each of the foot attachment parts 30 comprises a shoe 31, a reinforcement plate 32, and a support member 33. Meanwhile, in FIGS. 6A, 6B, and 6C the right foot attachment part 30R is depicted.

Meanwhile, the foot attachment parts 30 are one example of the "floor contact part" in the "DISCLOSURE OF TEE INVENTION."

The shoe 31 is a shoe contactably attached to a foot of the user P.

The reinforcement plate 32 is a resin member provided along outside of the foot of the user P, and is designed to be a structure of being able to transmit a floor reaction force received by the shoe 31 to the leg link part 20.

The support member 33 is a resin member for supporting the ankle joint part 25 in collaboration with the reinforcement plate 32. Meanwhile, the reinforcement plate 32 and the support member 33 may also be made of metal.

In the embodiment the leg link parts 20 and the foot attachment parts 30 have structures of being able to support part of the weight of the user P transmitted through the body attachment part 10.

In addition, at bottom of the shoe 31 is provided one of floor contact sensors 31a (left floor contact sensor 31aL, right floor contact sensor 31aR). The floor contact sensors 31a (31aL, 31aR) output an ON signal to the control unit 50 (see FIG. 7) during a floor contact.

The floor contact sensors 31a (31aL, 31aR) detect whether or not the foot attachment parts 30 has contacted the floor, and in the embodiment, are provided at foot bottoms of the foot attachment parts 30 (30L, 30R). The floor contact sensors 31a (31aL, 31aR) are one example of the "floor contact detection mechanism" in the "DISCLOSURE OF THE INVENTION."

In addition, the "floor" is not limited to a floor of a building and may be a face such as a ground surface which the foot attachment parts 30 contact when the user P with the body weight support device 1A moves (walks).

As the floor contact sensors 31a (31aL, 31aR), a sensor using a conductive rubber switch, a piezoelectric element, and a strain gauge is suitable. Although in the embodiment the floor contact sensors 31a (31aL, 31aR) for a one-axis detection are used, they may also use a floor contact sensor that can detect more than one axis. In addition, although in the embodiment the floor contact sensors 31a (31aL, 31aR) are provided at center portions of bottoms of the shoes 31, respectively, they may also be provided at heel portions, respectively. In addition, a plurality of floor contact sensors 31a may be provided at one of the shoes 31.

Although in the embodiment the upper thigh link parts 22 (22L, 22R) and the lower thigh link parts 24 (24L, 24R) are assumed to be aluminum members, they may also be formed of another material such as carbon that is lightweight and has a sufficient strength. In other words, the body attachment part 10, the leg link parts 20 (20L, 20R), and the foot attachment parts 30 (30L, 30R) may have a strength that can give a body weight support force to the user P by either left or right ones of the leg link parts 20 and the foot attachment parts 30, and a material thereof is appropriately selectable.

The backpack 40 is something which the user P shoulders and comprises the control unit 50 (see FIG. 7), an input/output interface 60 (see FIG. 7), and a battery (not shown). The control unit 50 will be described later in detail.

The input/output interface 60 connects an external computer and the like to the control unit 50. For example, personal data such as the weight of the user P is given to the control unit 50 from the external computer.

The battery supplies electric power to the load sensors 71a (71aL, 71aR), the crotch joint part actuators 21a (21aL, 21aR), the knee joint part actuators 23a (23aL, 23aR), the crotch joint part encoders 21b (21bL, 21bR), the knee joint part encoders 23b (23bL, 23bR), the floor contact sensors 31a (31aL, 31aR), and the control unit 50. The power supply by the battery is controlled by the control unit 50.

Meanwhile, the backpack 40 and the input/output interface 60 are not indispensable configuration requirements of the present invention. In other words, the attached mode of the control unit 50, the input/output interface 60, and the battery is not limited to one by the backpack 40, and such a mode of directly fitting them to the body attachment part 10 is also available.

Figure 7:
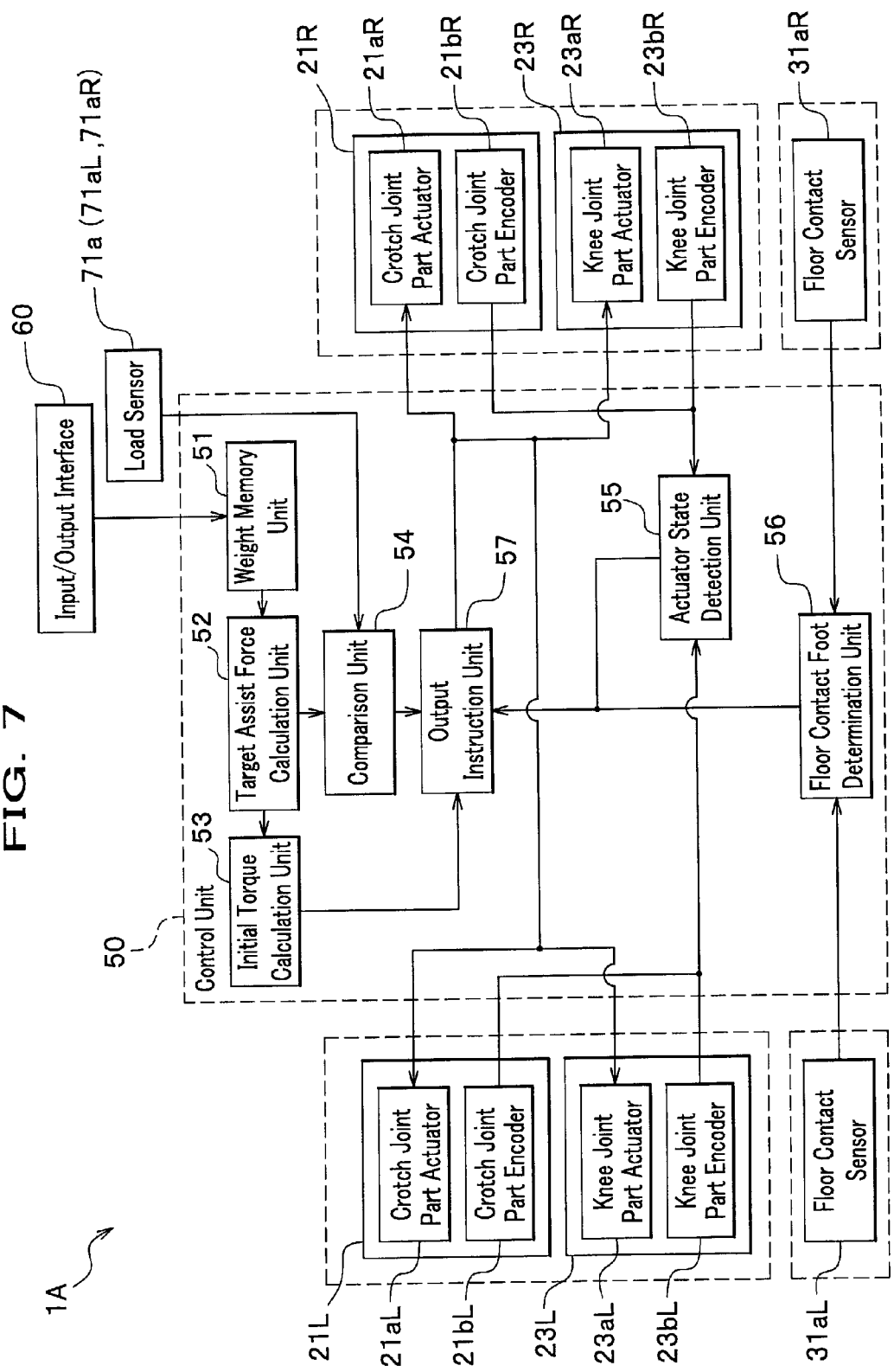
FIG. 7 is a block diagram showing a function of the body weight support device related to the embodiment of the present invention.

Subsequently, the control unit 50 will be described. FIG. 7 is a block diagram showing a function of the body weight support device 1A related to the embodiment of the present invention.

As shown in FIG. 7, the control unit 50 comprises a weight memory unit 51, a target assist force calculation unit 52, an initial torque value calculation unit 53, a comparison unit 54, an actuator state detection unit 55, a floor contact foot determination unit 56, and an output instruction unit 57.

The weight memory unit 51 obtains the weight (weight data) of the user P and memorizes (temporary memory) it. The weight may be input to the control unit 50 directly by the user P or the weight which the control unit 50 recognizing the user P has memorized in advance may be read from the weight memory unit 51. In addition, the weight may also be designed to be input to the weight memory unit 51 through the input/output interface 60 from the external computer. In addition, the weight memory unit 51 may also be designed to memorize only a value of the weight of the user P as the weight.

The target assist force calculation unit 52 reads the weight data memorized in the weight memory unit 51, and calculates a target body weight support force based on the weight data.

The "target body weight support force" is a target value of a force (a Z-axis positive direction on a horizontal floor in a standup state) given to the user P by the body weight support device 1A, and a predetermined ratio (for example, 30% of the weight) of the weight of the user P is set. In the embodiment, together with a target body weight support force Fa, are calculated a minimum body weight support force Fa1 and a maximum body weight support force Fa2. Here, the minimum body weight support force Fa1 corresponds to the "lower limit value of the target body weight support force" and the maximum body weight support force Fa2 corresponds to the "upper limit value, of the target body weight support force" in the "DISCLOSURE OF THE INVENTION."

For example, in a case of setting a support force of 30% of the weight as the target body weight support force Fa, a value of 28% of the weight is calculated as the minimum body weight support force Fa1; a value of 32% of the weight is calculated as the maximum body weight support force Fa2. These assist forces Fa, Fa1, and Fa2 are appropriately set according to a body weight support force wanted to be given to the user P, a calculation capacity, a characteristic of each of the actuators 21a and 23a, a characteristic of each of the sensors 11a and 31a, and the like.

A ratio setting of the target body weight support force Fa, the minimum body weight support force Fa1, and the maximum body weight support force Fa2 is appropriately changeable, and for example, it is enabled to set an arbitrary value from the external computer through the input/output interface 60.

The initial torque value calculation unit 53 calculates initial torque values to be given to the left crotch joint part actuator 21aL, the right crotch joint part actuator 21aR, the left knee joint part actuator 23aL, and the right knee joint part actuator 23aR, based on the target body weight support force Fa.

The initial torque values are calculated for each of three cases: (1) both-feet floor contact; (2) left-foot floor contact (right foot not in contact with the floor); and (3) right-foot floor contact (left foot not in contact with the floor).

In other words, (1) in the case of the both-feet floor contact are calculated initial torque values given to the left crotch joint part actuator 21aL, the right crotch joint part actuator 21aR, the left knee joint part actuator 23aL, and the right knee joint part actuator 23aR; (2) in the case of the left-foot floor contact are calculated initial torque values given to the left crotch joint part actuator 21aL and the left knee joint part actuator 23aL, and then those given to the right crotch joint part actuator 21aR and the right knee joint part actuator 23aR are zero; and (3) in the case of the right-foot floor contact are calculated initial torque values given to the right crotch joint part actuator 21aR and the right knee joint part actuator 23aR, and then those given to the left crotch joint part actuator 21aL and the left knee joint part actuator 23aL are zero.

These initial torque values are ones for improving an initial response of the body weight support device 1A, and it is preferable to make the values that enable the device 1A to transit to a state of bringing out the target body weight support force Fa smoothly and early from an initial state. By generating torques in each actuator of the initial state according to its initial torque value, even if the user P abruptly leaves her or his weight to the body weight support device 1A, it surely prevents the user P from falling down or losing her or his balance and thus can stably establish her or his standup state. Here, as the initial state can be cited an activation of the body weight support device 1A and a change (both-feet floor contact to one-foot floor contact and vice versa) of a floor contact state thereof.

In addition, giving the initial torque values also contribute to a prevention of a trouble of the body weight support device 1A.

Meanwhile, because torque values to be output by the actuators 21a and 23a change according to the assist forces Fa, Fa1, and Fa2 and rotation angles of the actuators 21a and 23a, the initial torque value may be designed to be set with also using a current rotation angle of each of the actuators 21a and 23a.

The comparison unit 54 compares a body weight support force Fb (hereinafter simply referred to as "load Fb" if necessary) at present time, based on a detection load of the load sensors 71a (71aL, 71aR) with a calculation result of the target assist force calculation unit 52. The comparison unit 54 memorizes a relationship between an actual detection value by the load sensors 71a (71aL, 71aR) and a body weight support force by the leg link parts 20 in the actual detection value. Accordingly, the comparison unit 54 can obtain the body weight support force Fb actually acting, based on a detection result of the load sensors 71a (71aL, 71aR).

As a comparison result, there are three results: (11) Fb<Fa1; (12) Fa1≦Fb≦Fa2; and (13) Fb>Fa2. The comparison result is output to the output instruction unit 57.

Based on output from the left crotch joint part encoder 21bL, the right crotch joint part encoder 21bR, the left knee joint part encoder 23bL, and the right knee joint part encoder 23bR, the actuator state detection unit 55 detects a state of each of these joint parts. The detection result is output to the output instruction unit 57.

The floor contact foot determination unit 56 determines in which state of (1) both-feet floor contact, (2) left-foot floor contact, or (3) right-foot floor contact a floor contact foot is.

In other words, the floor contact foot determination unit 56 determines that: a case of there being output from both of the left floor contact sensor 31aL and the right floor contact sensor 31aR is (1) a state of both-feet floor contact; a case of there being output only from the left floor contact sensor 31aL is (2) a state of left-foot floor contact (right foot not in contact with the floor); and a case of there being output only from the right floor contact sensor 31aR is (1) a state of right-foot floor contact (left foot not in contact with the floor). The determination result is output to the output instruction unit 57.

The output instruction unit 57 decides and instructs output of each of the actuators 21aL, 21aR, 23aL, and 23aR, based on the calculation result of the initial torque value calculation unit 53, the comparison result of the comparison unit 54, the detection result of the actuator state detection unit 55, and the determination result of the floor contact foot determination unit 56.

The output instruction unit 57 expects a behavior of the leg link parts 20 (20L, 20R), based on the detection results of the actuator state detection unit 55 and these variation amounts, and decides the output of each of the actuators 21aL, 21aR, 23aL, and 23aR, based on the expectation result.

Figure 13A:
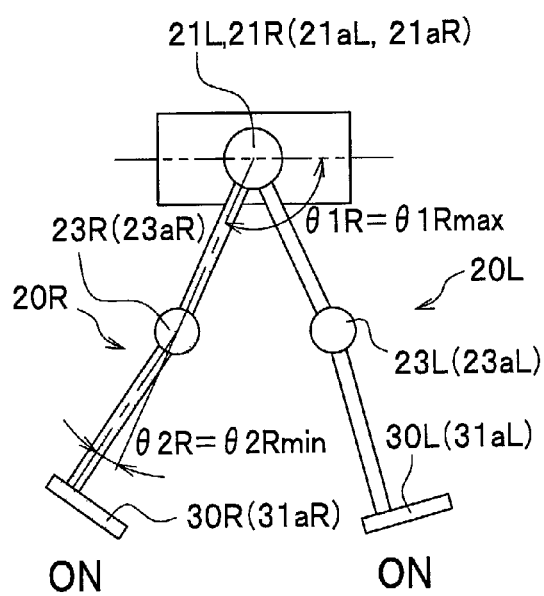
FIGS. 13A to 13D are drawings showing a state transition of a right leg link part in a user's walking.

For example, in FIG. 13A described later, when an angle θ1R becomes large enough and nears a predetermined value (for example, set in an angle at timing when the right foot is separated from the floor last time), it is expected that the right foot will soon separate from the floor. In other words, the control unit 50 obtains and memorizes an angle θ1 (floor separation angle: corresponding to a rotation angle of the crotch joint part actuators 21a) at timing when a foot is separated from the floor. Then the control unit 50 expects the behavior of a leg of the user P, using the floor separation angle θ1.

Thus by moving the ratio of the body weight support force Fb to the left leg link part 20L, the right foot becomes in the air and can prepare (smooth transfer of a torque output fluctuation of the actuators) a state of having to support his weight only by a left system (the body attachment part 10, the left leg link part 20L, and the left foot attachment part 30L), and realize a more stable body weight support.

[Torque Generation Direction]

Figure 8A:
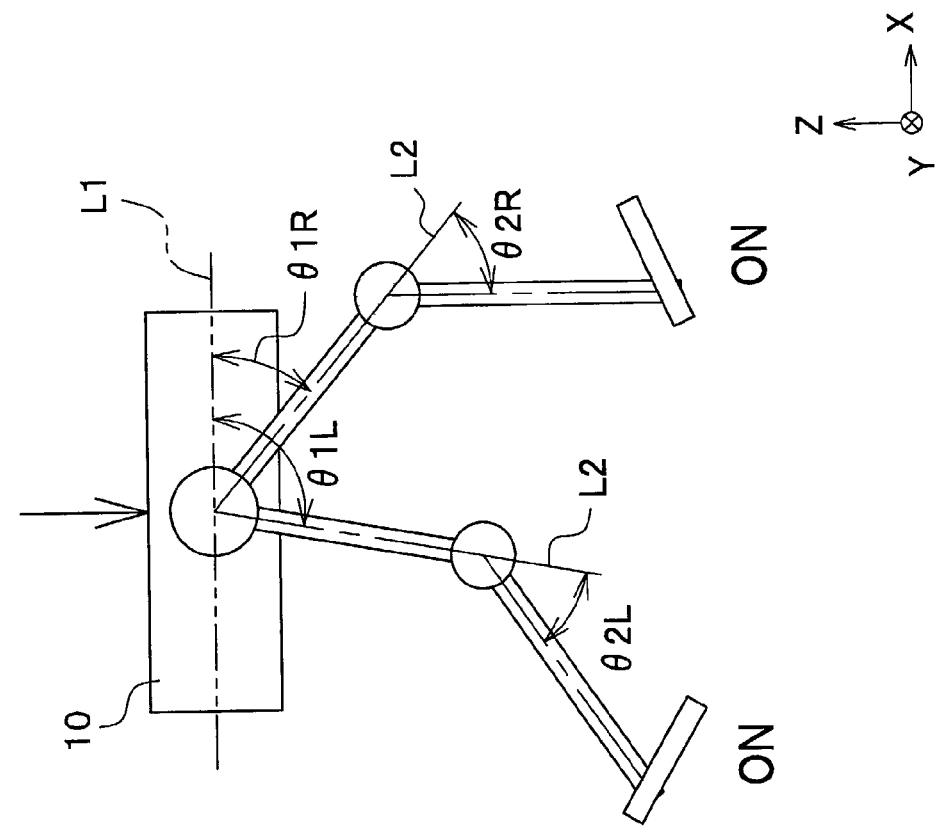
FIGS. 8A and 8B are drawings illustrating a torque generation direction by a crotch joint part actuator and a knee joint part actuator.
Figure 8B:
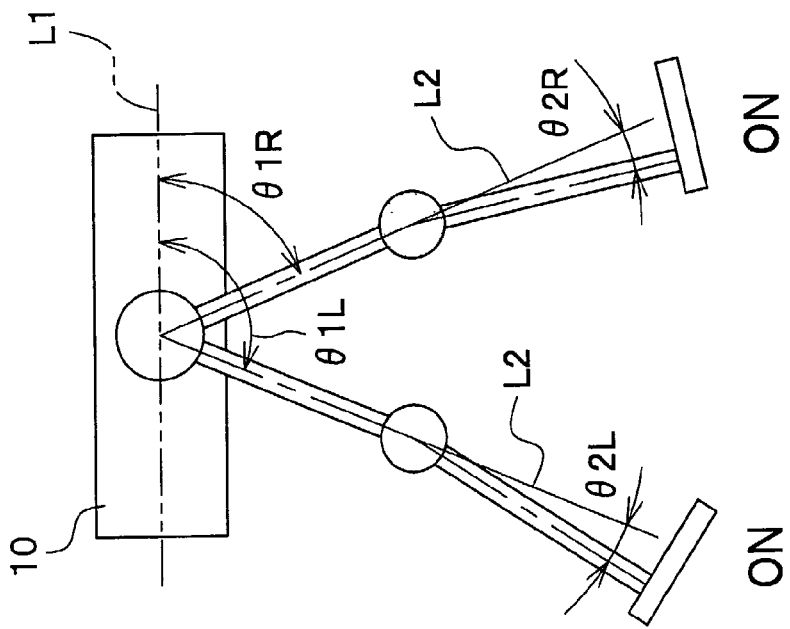

Subsequently, a torque generation direction of the crotch joint part actuators 21a (21aL, 21aR) and the knee joint part actuators 23a (23aL, 23aR) will be described. FIGS. 8A and 8B are drawings illustrating a torque generation direction by a crotch joint part actuator and a knee joint part actuator; FIG. 8A is a schematic drawing showing a state of a torque being sufficiently generated; and FIG. 8B is a schematic drawing showing a state of torque being insufficient and a user becoming such a state of losing her or his balance. Meanwhile, in drawings below, "ON" in the drawings indicates the foot attachment parts 30 (30L, 30R) are in contact with the floor, "OFF" indicates the foot attachment parts 30 (30L, 30R) are not in contact with the floor.

In FIGS. 8A and 8B a line L1 is a horizontal line along the waist belt part 11; lines 2 are lines extending in a longitudinal direction of the upper thigh link parts 22 (22L, 22R); angles θ1 (θ1L, θ1R) are ones made by the line L1 and the upper thigh link parts 22; and angles θ2 (θ2L, θ2R) are ones made by the lines L2 and the lower thigh link parts 24 (24L, 24R).

As shown in FIG. 8A, in a case of the body weight support device 1A bringing out a sufficient body weight support force, the user P can keep a standup state even if she or he does not support the whole weight by her or his own legs.

But as shown in FIG. 8B, in a case of a leg force of the user P is insufficient and the body weight support device 1A not bringing out the sufficient body weight support force, the device 1A change a posture of the user P so that the angles θ1 (θ1L, θ1R) become smaller and the angles θ2 (θ2L, θ2R) become larger.

In other words, in order to bring out the sufficient body weight support force, the body weight support device 1A may respectively generate torques in such a direction that the crotch joint part actuators 21a (21aL, 21aR) make the angles θ1 (θ1L, θ1R) larger, and in such a direction that the knee joint part actuators 23a (23aL, 23aR) make the angles θ2 (θ2L, θ2R) smaller.

Meanwhile, each of the actuators 21a and 23a are controlled so that a movable range of each of the joint parts 21 and 23 does not exceed at least that of joint parts of an ordinary human being. Therefore, safety is further improved. In addition, the upper thigh link parts 22, the knee joint parts 23 (knee joint part actuators 23a), and the lower thigh link parts 24 are adjusted in length thereof so that the upper thigh link parts 22 and the lower thigh link parts 24 do not become in line (not fully elongated) and so that the knee joint parts 23 always become a bent state (avoidance of a singular point, see FIGS. 3 and 4). In other words, the body weight support device 1A is designed to be a structure of surely preventing the upper thigh link parts 22 and the lower thigh link parts 24 from becoming in line and bending to a reverse side. Thus an impact to the attachment parts (body attachment part 10, foot attachment parts 30) is alleviated and a controllability of a weight relief amount by the actuators 21a and 23a is improved. Meanwhile, in order to surely restrict the movable range of the actuators 21a and 23a, a mechanical stopper may be provided at each of the actuators 21 and 23 and each of the link parts 22 and 24.

[Relationship Between Generation Torque and Body Weight Support Force]

Subsequently, a relationship between a generation torque and a body weight support force will be described.

FIGS. 9 and 10 are drawings illustrating a relationship between a generation torque and a body weight support force; FIG. 9 is a drawing illustrating a relationship between a generation torque of a knee joint part actuator and a body weight support force; and FIG. 10 is a drawing illustrating a relationship between a generation torque of a crotch joint part actuator and a body weight support force.

Firstly, referring to FIG. 9, a relationship between a generation torque of the right knee joint part actuator 23aR and a body weight support force will be described. Here, it is assumed that the right crotch joint part actuator 21aR is unrotatably fixed.

If the right foot attachment part 30R contacts a floor and the right knee joint part actuator 23aR generates a torque in a direction of lessening the angle θ2R, a rotation force is given to the right crotch joint part actuator 21aR in a tangential direction of a circle making the actuator 23aR a center. An anti-gravity direction (Z-axis direction) component of the rotation force is a body weight support force Fa1R by the right knee joint part actuator 23aR.

Subsequently, referring to FIG. 10, a relationship between a generation torque of the right crotch joint part actuator 21aR and a body weight support force will be described. Here, it is assumed that the right knee joint part actuator 23aR is unrotatably fixed.

If the right foot attachment part 30R contacts the floor and the right crotch joint part actuator 21aR generates a torque in a direction of enlarging the angle θ1R, a rotation force is given to the body attachment part 10 in a tangential direction of a circle making the actuator 21aR a center. The anti-gravity direction (Z-axis direction) component of the rotation force is a body weight support force Fa2R by the right crotch joint part actuator 21aR.

Meanwhile, although not shown, a body weight support force Fa1L by the left knee joint part actuator 23aL and a body weight support force Fa2L by the left crotch joint part actuator 21aL are generated appropriately, a target body weight support force (total assist force) Fa by the body weight support device 1A is expressed by following equations:

(1) both-feet floor contact $$Fa=Fa1R+Fa2R+Fa1L+Fa2L;$$

(2) left-foot floor contact $$Fa=Fa1L+Fa2L;\ \text{and}$$

(3) right-foot floor contact $$Fa=Fa1R+Fa2R.$$

[Load of Foot Attachment Parts]

Figure 11:
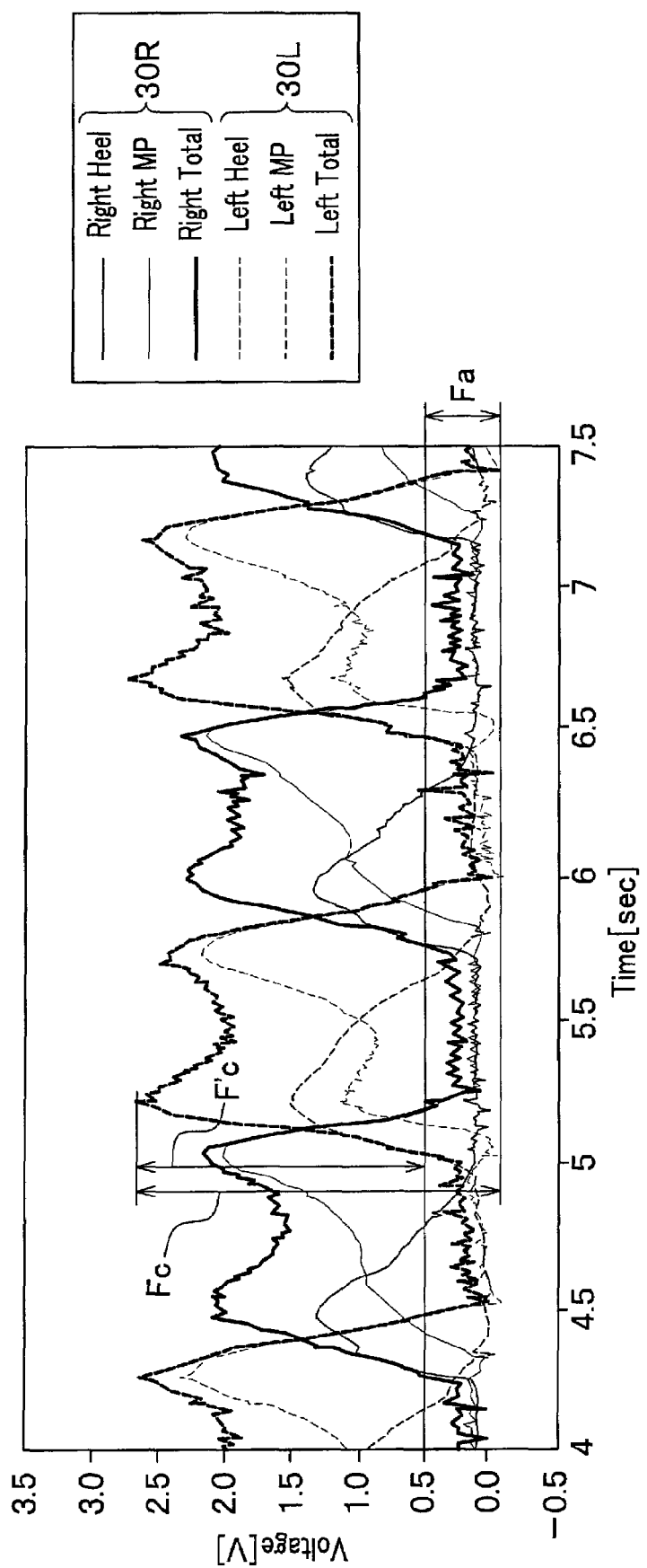
FIG. 11 is a graph showing a result of measuring a pressure loaded on foot attachment parts in walking.

Subsequently, a load on the foot attachment parts 30 (30L, 30R) will be described. FIG. 11 is a graph showing a result of measuring a pressure loaded on the foot attachment parts 30 (30L, 30R) in walking. A transition of the pressure in walking and an effect of the body weight support device 1A can be explained by FIG. 11. In a state that pressure sensors were attached to two places (heel portion and position of metatarsophalangeal joint of a foot of a leg [MP] [joint of a root of thumb of a foot]) of bottom sides of the foot attachment parts 30 (30L, 30R) of the body weight support device 1A, the user P put on the device 1A and walked Output of the pressure sensors is indicated in voltage. While the user P walked, it is turned out that an appearance of the load transiting alternately in the left foot attachment part 30L and the right foot attachment part 30R from a heel to a foot tip thereof. The body weight support device 1A gives the body weight support force Fa to the user P, thereby reduces a maximum load (Fc to Fc') on her or his feet, and facilitates walking.

[Operation Example of Body Weight Support Device]

Figure 12:
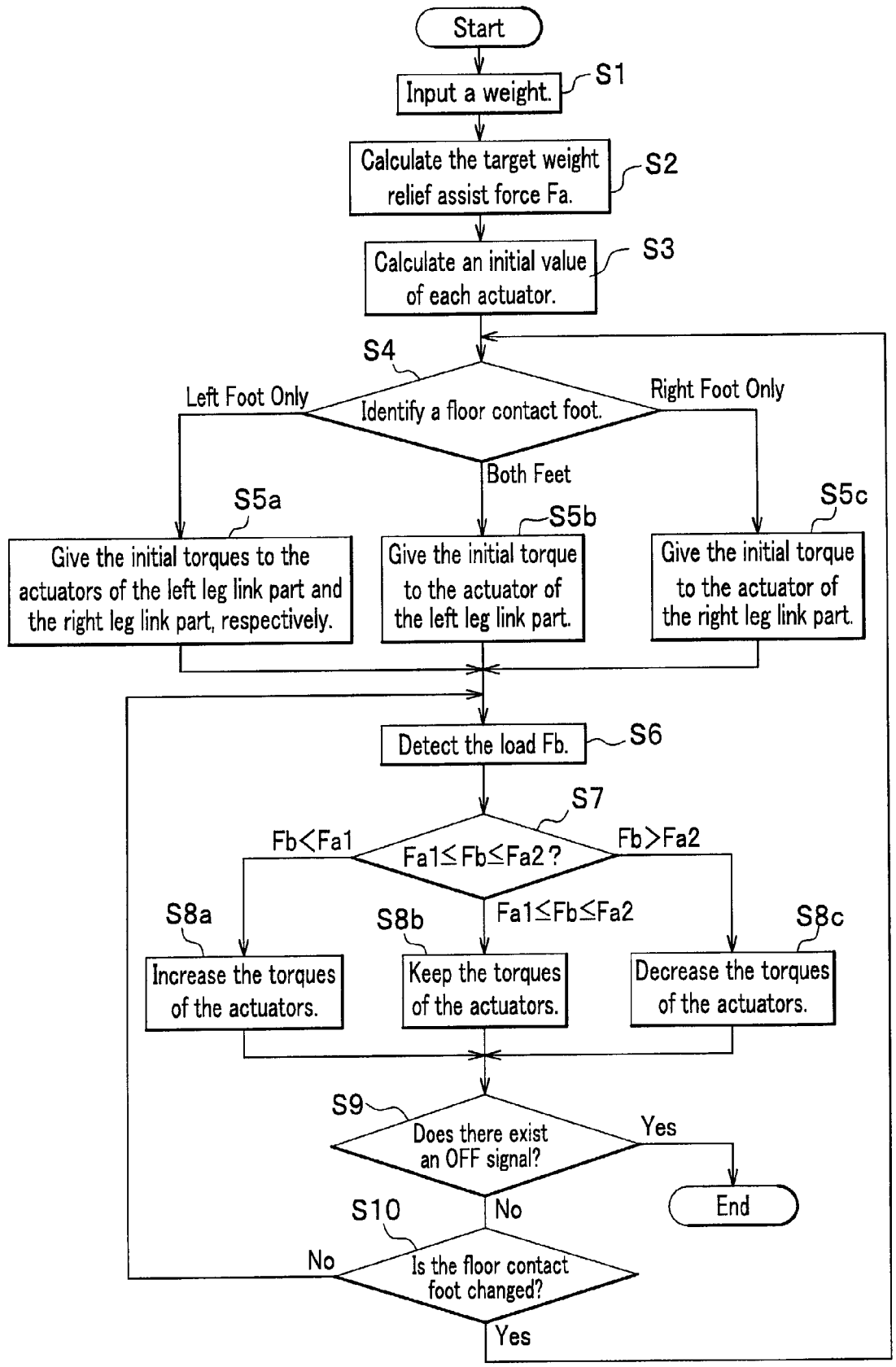
FIG. 12 is a flowchart showing an operation example of the body weight support device related to the embodiment of the present invention.

Subsequently, an operation example of the body weight support device 1A will be described. FIG. 12 is a flowchart showing the operation example of the body weight support device 1A related to the embodiment of the present invention.

Firstly, in a state of the user P having put on the body weight support device 1A, the weight of the user P is input. The weight input is memorized in the weight memory unit 51 (step S1).

Subsequently, the target assist force calculation unit 52 calculates the target body weight support force Fa (Fa1, Fa2), based on the weight of the user P memorized in the weight memory unit 51 (step S2).

Subsequently, the initial torque value calculation unit 53 calculates an initial torque value, based on the target body weight support force Fa (step S3).

Subsequently, the floor contact foot determination unit 56 identifies a floor contact foot, based on the output of floor contact sensors 31a (step S4).

If it is determined that the floor contact foot is only the left foot, the output instruction unit 57 drives the left crotch joint part actuator 21aL and the left knee joint part actuator 23aL so as to generate a torque depending on the initial torque value (step S5a).

If it is determined that the floor contact foot is both feet, the output instruction unit 57 drives the left crotch joint part actuator 21aL, the right crotch joint part actuator 21aR, the left knee joint part actuator 23aL, and the right knee joint part actuator 23aR so as to generate a torque depending on the initial torque value (step S5b).

If it is determined that the floor contact foot is only the right foot, the output instruction unit 57 drives the right crotch joint part actuator 21aR and the right knee joint part actuator 23aR so as to generate a torque depending on the initial torque value (step S5c).

Subsequently, the load sensors 71a detect the load Fb (step S6), and the comparison unit 54 compares the detected load Fb with the calculated target body weight support force Fa (Fa1, Fa2) (step S7). Meanwhile, a detection value itself by the load sensors 71a may be simply compared to a threshold value of the detection value converted based on the calculated target body weight support force Fa.

If the load Fb is less than Fa1, the output instruction unit 57 increases a current amount to the actuators of a floor contact foot by a predetermined amount, and thus increases a generation torque by a predetermined amount (step 8a).

If the load Fb is not less than Fa1 and not more than Fa2, the output instruction unit 57 keeps the torque of the actuators of the floor contact foot (step 8b).

If the load Fb exceeds Fa2, the output instruction unit 57 decreases the current amount of the floor contact foot by a predetermined amount, and thus decreases a generation torque by a predetermined amount (step 8c).

Meanwhile, the predetermined amount for the increase/decrease of the current is appropriately set according to a calculation capacity of the control unit 50, a characteristic of each of the actuators 21a and 23a, and that of each of the sensors 71a and 31a.

Subsequently, if an OFF signal is input to the control unit 50 (Yes in step S9), the body weight support device 1A ends the processing. If the OFF signal is not input to the control unit 50 (No in the step S9), the floor contact foot determination unit 56 determines whether or not there exists a change of the floor contact foot (step S10).

If it is determined that there exists the change of the floor contact foot (both-feet floor contact to one-foot floor contact and vice versa) (Yes in the step S10), is transit to the step S4. In addition, if it is determined that there does not exist the change of the floor contact foot (No in the step S10), transit to the step S6.

[State Transition and Torque Generation of Leg Link Parts]

Subsequently, a state transition of the body weight support device 1A accompanied with the user P walking will be described, particularly taking notice of a state transition of the right leg part 20R. FIGS. 13A to 13D and 14A to 14C are drawings illustrating a state transition of the angle θ1R and angle θ2R of the right leg link part R in the user P walking.

Meanwhile, a walking mode is different in every user P and a knee angle in walking is also different in her or him. One example thereof is shown in FIGS. 13A to 13D and 14A to 14C.

When the right leg of the user P is positioned at a most rear position (FIG. 13A, a state 1), the right upper thigh link part 22R and the right lower thigh link part 24R become almost in line. At this time the angle θ1R becomes maximum (θ1R=θ1Rmax), and the angle θ2R becomes minimum (θ2R=θ2Rmin). Here, because the right foot attachment part 30R contacts the floor, the right crotch joint part actuator 21aR generates a torque in a direction of enlarging the angle θ1R, and the right knee joint part actuator 23aR generates a torque in a direction of lessening the angle θ2R.

Figure 13B:
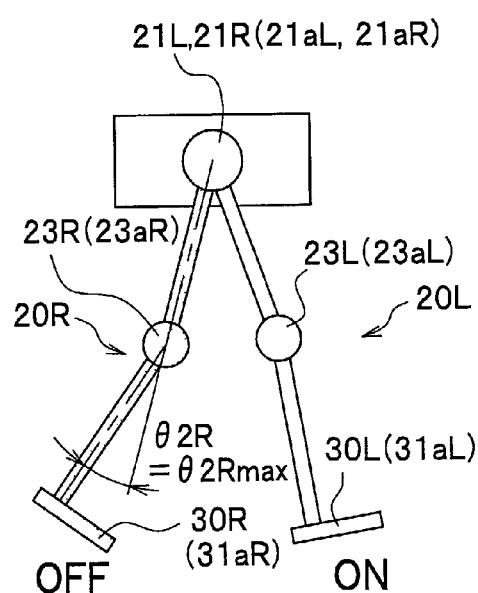

If the user P swings forward (in the X-axis positive direction) her or his right leg, the right leg (right foot attachment part 30) is separated from the floor. Here, the generation torque of the right crotch joint part actuator 21aR and the right knee joint part actuator 23aR becomes "zero." After the separation of the right leg, because the angle θ1R gradually becomes smaller and the right foot attachment part 30R follows the knee joint part 23R with delaying for it, the angle θ2R becomes larger for some time, and in a state of the angle θ2R having become maximum (θ2R=θ2Rmax), the part 23R continues on being swung forward (FIG. 13B, a state 2).

Figure 13C:
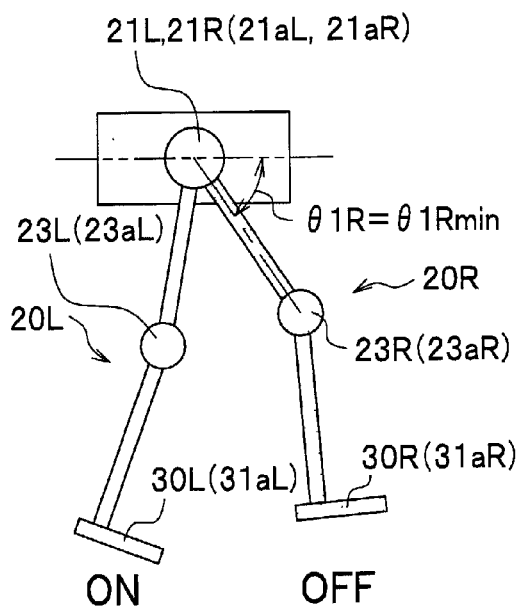
Figure 13D:
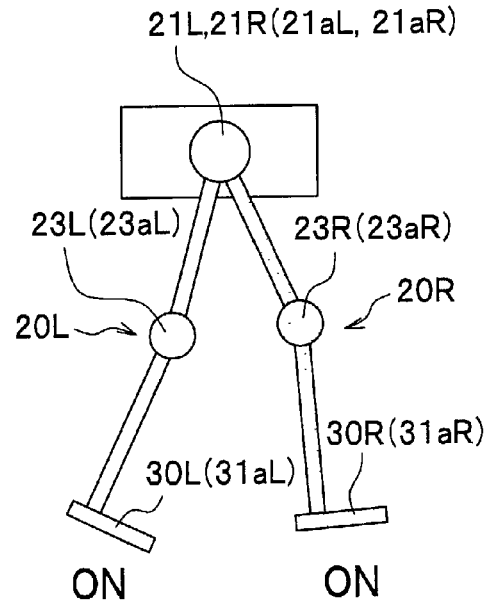

If the user P continues on swinging forward the right leg from the state 2, the angle θ1R becomes minimum (θ1R=θ1Rmin) (FIG. 13C, a state 3). Thereafter, because although the angle θ1R gradually becomes larger, the foot attachment part 30R comes forward with delaying for the knee joint part 23R, the angle θ2R gradually becomes smaller, and the foot attachment part 30R contacts the floor (FIG. 13D, a state 4). Thereafter, while the left leg performs the above described operation similar to the right leg (FIG. 14A, a state 5; FIG. 14B, a state 6; and FIG. 14C, a state 7 (=the state 1)), that is, when the right leg contacts the floor, the right crotch joint part actuator 21aR generates a torque in a direction of always enlarging the angle θ1R, and the right knee joint part actuator 23aR generates a torque in a direction of always lessening the angle θ2R.

Meanwhile, it is also available to design in a leg being in the air so that each of the crotch joint part actuators 21a generates a torque in a counterclockwise direction in FIGS. 13A to 13D, and thus gives the assist force Fa (Fa1, Fat) to the upper thigh of the user P for the swinging-forward operation.

In accordance with the body weight support device 1A following effects can be obtained.
(1) Because the body weight support device 1A supports part of the weight of the user P, it can reduce a load on her or his legs accompanying her or his weight support.
(2) Because the body weight support device 1A detects a load on herself or himself and supports a definite ratio of her or his weight, based on the load, it can perform a support corresponding to her or his posture change and the like.
(3) Because the body weight support device 1A gives a body weight support force only to a floor contact foot, it can give a suitable body weight support force accompanied with the change of a walking posture and dose not interrupt the operation of a leg not in contact with the floor.
(4) Because different from a stick (crutches, a four-point support stick, and the like) the body weight support device 1A does not need an operation by the hands of the user P, she or he can use the hands even during a walking assist. In addition, there is no possibility of her or his arms and upper body becoming tired, accompanied with a long time use thereof;

(5) Because the body weight support device 1A has a compact configuration along with the legs of the user P, it does not become an obstacle even in moving a narrow passage, staircases, and the like. In addition, because a configuration of each of the actuators 21a and 23a and the link parts 22 and 24 is analogous to a mechanism of a human lower limb, and these are arranged along the limbs (legs) of the user P, the configuration tends more to synchronize a human walking operation and is better in a transmission efficiency of the body weight support force than a configuration using a directly moved actuator and an assist device of a configuration of being separated from the lower limbs of the user P.
(6) Because the body weight support device 1A does not need a wheel, it can be used without depending on a floor condition.
(7) The body weight support device 1A has less constraint regions in the user P, it is suitable for a long time use. In other words, different from a conventional walking aid device, because the device 1A related to the embodiment of the present invention does not need the constraint of such knees and upper thighs and can almost do without the constraint of the legs of the user P, she or he does not feel an uncomfortable constraint and ache. In addition, the body weight support device 1A does with less constraint regions, it can be lighter weight, various users can use the body weight support device 1A of one type, and thus the device 1A results in being very high in versatility.
(8) In addition, the body weight support device 1A also has a feature that a portion (attachment portion of the crotch joint part actuators 21a) where the body weight support force is given to the user P from the device 1A and a portion (upper thigh portion and groin portion of the body attachment part 10) where she or he leaves her or his weight are positioned within a substantially same vertical plane (Y-Z plane in FIGS. 3 and 4. By making such the configuration, it is prevented to generate an unnecessary moment in the user P in a pitch direction (around the Y-axis) when performing a body weight support.

VARIATION EXAMPLE

Subsequently, concerning variation examples of the body attachment part 10 will be mainly described a difference from the body weight support device 1A. FIGS. 15A, 15B, and 15C are drawings showing the variation examples of the body attachment part 10. Meanwhile, in the FIGS. 15A to 15C each backpack 40 is omitted.

A body attachment part 110 of a body weight support device 1B shown in FIG. 15A comprises a waist belt part 11, actuator attachment parts 13L and 13R, crotch belt parts 112L and 112R. The crotch belt parts 112L and 112R are cloth members put around the crotch of the user P and are connected to the actuator attachment parts 13L and 13R, respectively.

The body weight support device 1B is realized to be lightweight by making the belt of the body attachment part 10 simpler than the body weight support device 1A shown in FIG. 1.

A body attachment part 210 of the body weight support device 1C shown in FIG. 15B comprises the waist belt part 11, the actuator attachment parts 13L and 13R, upper thigh belt parts 212L and 212R. The upper thigh belt parts 212L and 212R are cloth members put around the upper thighs of the user P and are connected to the actuator attachment parts 13L and 13R, respectively.

The body weight support device 1C is an example of heightening a support function in the upper thighs of the user P more than the body weight support device 1B and instead alleviating a stress in her or his groin portion.

A body attachment part 310 of the body weight support device 1D shown in FIG. 15C comprises the waist belt part 11, the actuator attachment parts 13L and 13R, armpit support parts 312L and 312R. The armpit support parts 312L and 312R are members for supporting the armpits of the user P and are connected to the actuator attachment parts 13L and 13R, respectively. The armpit support parts 312L and 312R, the actuator attachment parts 13L and 13R, the leg link parts 20L and 20R, the foot attachment parts 30L and 30R have a structure of being able to support a load on the armpit support parts 312L and 312R.

The body weight support device 1D is an example suitable for the user P that is difficult to constrain her or his upper thighs and groin portion due to a disease, an injury, and the like.

Other than these is also available such a device configuration where a body weight support force by a body weight support device is given to a jaw portion of the user P.

Figure 16:
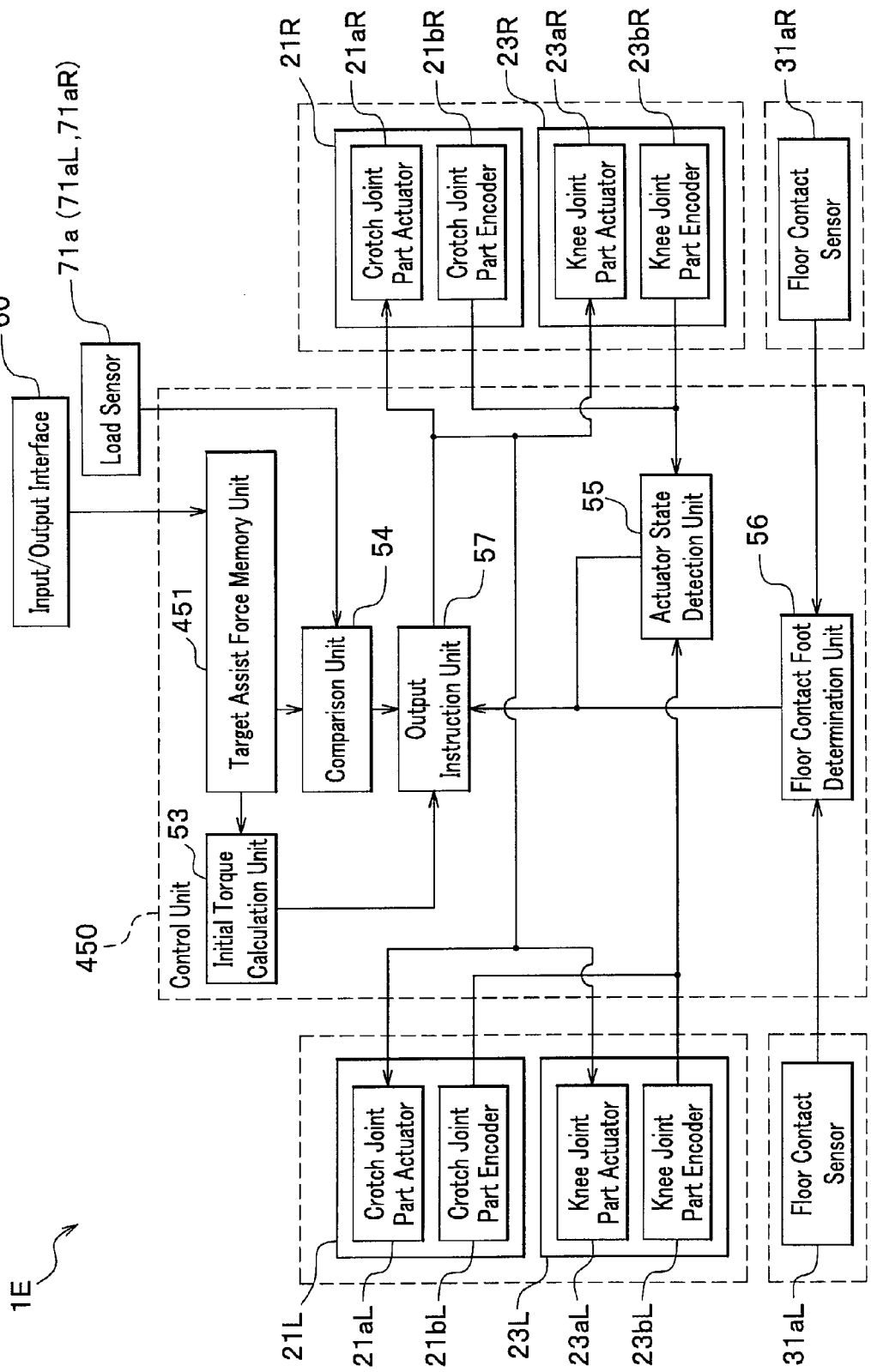
FIG. 16 is a block diagram showing a variation example of a control unit.

Subsequently, concerning a variation example of the control unit 50 will be mainly described a difference from the body weight support device 1A. FIG. 16 is a block diagram showing the variation example of the control unit 50.

A control unit 450 of a body weight support device 1E shown in FIG. 16 comprises a target assist force memory unit 451 instead of the weight memory unit 51 and the target assist force calculation unit 52.

The target assist force memory unit 451 memorizes the target body weight support force Fa (for example, 10 kg) of a predetermined value set in advance. In addition, the target assist force memory unit 451 memorizes the minimum body weight support force Fa1 (for example, 9 kg) and the maximum body weight support force Fa2 (for example, 11 kg) corresponding to the target body weight support force Fa. In an operation flow of such the body weight support device 1E is calculated an initial torque value using these values, and a torque of an actuator is controlled.

Although the embodiment of the present invention is described, referring to the drawings, the invention is not limited thereto and the embodiment is appropriately changeable in design without departing the spirit and scope of the invention.

(1) Although each of the above mentioned body weight support devices is designed to integrate a joint part and an actuator, they may be designed to be separate bodies and to transmit a drive force of the actuator to the joint part through a drive force transmission mechanism comprising a link mechanism, a belt, and the like.

(2) The body weight support device may also be designed to omit a crotch joint part actuator and to drive the joint part only by a knee joint part actuator. In this case are realized the lightweight of the body weight support device and the simplification of the control.

(3) Although the body weight support device is designed to arrange each actuator and each link part along outside of a user's limb, all actuators and link parts or at least one of them may also be arranged inside the user's lower limb.

(4) The body weight support device may also be such a configuration that each foot attachment part is omitted and a lower end of a lower thigh link part contacts a floor. In this case, while synchronizing the body weight support device with a walking operation of a user by providing a lower limb attachment part, which is connected to a leg link part instead of her or his foot constraint by the foot attachment part and is attached to any of an ankle, a lower thigh, a knee, and a upper thigh, body weight support control is enabled by detecting a floor contact foot with a floor contact sensor provided at any of her or his foot bottom and a lower end of the lower thigh link part.

(5) Although in the control flow of FIG. 12 a case is described as an example that the control unit 50 performs processing according to a program (body weight support program) stored in advance, the program may also be designed to be provided in the body weight support device from outside by a recording medium and a network.

(6) Although each of the body weight support devices is provided in both lower limbs of a user, it may also be a configuration of being provided in either one of the right or left limb. For example, in a case that a function of only one foot of the user is lowered, a body weight support force can be given by providing the body weight support device only in the lower limb whose function is lowered.

INDUSTRIAL APPLICABILITY

In accordance with the present invention can be realized a body weight support device that can alleviate the constraint of legs of a user, is lightweight, can reduce a load on the legs, and fits each user well according to a body type and a way in walking, and a body weight support program therefor.

The invention claimed is:
1. A body weight support device comprising:
a body attachment part attached to a body of a user;
a floor contact part provided contactably on a floor,
a leg part including an upper thigh link part, a knee joint part, and a lower thigh link part for connecting said body attachment part to said floor contact part through a joint part including the knee joint part, the upper thigh link part, the knee joint part, and the lower thigh link part being adjusted in length to prevent the upper thigh link part and the lower thigh link part from becoming in line and bending to a reverse side when the user wears the body weight support device;
an actuator for driving said joint part; and
a control unit for controlling driving of said actuator,
said control unit driving said actuator to produce rotational power at the knee joint part, so that said leg link part gives a body weight support force to said user through said body attachment part, the body weight support force being a force for partially supporting weight of the user, and
the leg link part is provided not to exert the body weight support force directly on upper or lower thighs or knee joints of the user while the user is wearing said body weight support device, and the leg link part is kept bent while the user is wearing said body weight support device,
wherein, when the user swings forward a leg of the user, the foot attachment is delayed relative to the knee joint part.
2. The body weight support device according to claim 1,
wherein the leg link part comprises the knee joint part, an upper thigh link part and an lower thigh link part, the upper thigh link part being coupled to the body attachment part and to the knee joint part, the lower thigh link part being coupled to the floor contact part and to the knee joint part, and
wherein the leg link part bends at the knee joint part only in the same direction as a leg of the user does when the user wears said body weight support device.

3. The body weight support device according to claim 2, wherein said actuator comprises a knee joint part actuator for driving the knee joint part, and wherein said leg link part and said knee joint part actuator are provided along the leg of said user.

4. The body weight support device according to claim 1, wherein the leg link part is provided on the upper or lower thighs or the knee joints of the user in such a way that the leg link part does not fasten the upper or lower thighs or the knee joints of the user while the user is wearing said body weight support device.

5. The body weight support device according to claim 1, further comprising a stopper being provided in the leg link part or the actuator,
wherein the stopper allows the leg link part not to be stretched or not to bend to a reverse side while the user is wearing said body weight support device.

6. The body weight support device according to claim 1, wherein at least part of the leg link part is provided outside the leg of the user.

7. The body weight support device according to claim 1 that further comprises a floor contact detection mechanism for detecting a user's foot contact with a floor,
wherein if said floor contact detection mechanism detects the floor contact, said control unit drives said actuator so that said leg link part gives said body weight support force to said user.

8. The body weight support device according to claim 7, wherein if said floor contact detection mechanism does not detect the floor contact, said control unit terminates driving of said actuator and makes said joint part rotation-free.

9. The body weight support device according to claim 1, further comprising:
a leg link part behavior detection mechanism for detecting a behavior of the leg link part,
wherein the control unit predicts that the contact between the floor and the leg of the user is to be released based on the detection result of the leg link part behavior detection mechanism, and the control unit decreases the body weight support force produced by the leg link part, before the leg of the user comes off the floor.

10. The body weight support device according to claim 9, further comprising:
a floor contact detection mechanism for detecting contact between a floor and the leg of the user,
wherein the control unit predicts that the contact between the floor and the leg of the user is to be released based on the detection results of the floor contact detection mechanism and the leg link part behavior detection mechanism, and the control unit decreases the body weight support force produced by the leg link part, before the leg of the user comes off the floor.

11. The body weight support device according to claim 1, wherein the actuator is controlled so that a movable range of the knee joint parts does not exceed at least that of the knee joint part of the user.

12. A body weight support device comprising
a body attachment part attached to a body of a user;
a floor contact part provided contactably on a floor;
a leg link part including an upper thigh link part, a knee joint part, and a lower thigh link part for connecting said body attachment part to said floor contact part through a joint part including the knee joint part, the upper thigh link part, the knee joint part, and the lower thigh link part being adjusted in length to prevent the upper thigh link part and the lower thigh link part from becoming in line and bending to a reverse side when the user wears the body weight support device;
an actuator for driving said joint part;
a control unit for controlling driving of said actuator; and
said control unit driving said actuator to produce rotational power at the knee joint part, so that said leg link part gives a body weight support force to said user through said body attachment part, the body weight support force being a force for partially supporting weight of the user;
the leg link part being provided not to exert the body weight support force directly on upper or lower thighs or knee joints of the user while the user is wearing said body weight support device;
a floor contact detection mechanism for detecting a user's foot contact with a floor, wherein if said floor contact detection mechanism detects the floor contact, said control unit drives said actuator so that said leg link part gives said body weight support force to said user;
said actuator comprising a crotch joint part actuator for driving a crotch joint part provided in said leg link part, and wherein if said floor contact detection mechanism does not detect the floor contact, said control unit drives said crotch joint part actuator so as to assist an upper thigh of said user to swing forward,
wherein, when the user swings forward a leg of the user, the foot attachment is delayed relative to the knee joint part.

13. The body weight support device according to claim 12, wherein the actuator is controlled so that a movable range of the knee joint parts does not exceed at least that of the knee joint part of the user.

14. A body weight support device comprising:
a body attachment part attached to a body of a user;
a floor contact part provided contactably on a floor;
a leg link part including an upper thigh link part, a knee joint part, and a lower thigh link part for connecting said body attachment part to said floor contact part through a joint part including the knee joint part, the upper thigh link part, the knee joint part, and the lower thigh link part being adjusted in length to prevent the upper thigh link part and the lower thigh link part from becoming in line and bending to a reverse side when the user wears the body weight support device;
an actuator for driving said joint part;
a control unit for controlling driving of said actuator,
said control unit driving said actuator to produce rotational power at the knee joint part, so that said leg link part gives a body weight support force to said user through said body attachment part, the body weight support force being a force for partially supporting weight of the user,
the leg link part being provided not to exert the body weight support force directly on upper or lower thighs or knee joints of the user while the user is wearing said body weight support device;
a floor contact detection mechanism for detecting a user's foot contact with a floor, wherein if said floor contact detection mechanism detects the floor contact, said control unit drives said actuator so that said leg link part gives said body weight support force to said user; and
wherein in said control unit, a predetermined value of a target body weight support force is set, and wherein if said floor contact detection mechanism detects the floor contact, said control unit drives said actuator so that said leg link part gives said target body weight support force to said user,
a load detection mechanism for detecting a load of said user on said leg link part through said body attachment part, wherein in said control unit, a lower limit value and an upper limit value of said target body weight support force are set, and said control unit drives said actuator so that the body weight support force by said leg link part falls between said lower and upper limit values of said target body weight support force, based on the load detected by said load detection mechanism.

15. The body weight support device according to claim 14, wherein in said control unit, the target body weight support force is set to have a predetermined ratio of a weight of said user.

16. The body weight support device according to claim 14, wherein the actuator is controlled so that a movable range of the knee joint parts does not exceed at least that of the knee joint part of the user.

17. The body weight support device according to claim 1, 12 or 14 that further comprises a load detection mechanism for detecting a load of said user on said leg link part through said body attachment part,
wherein said control unit drives said actuator, based on said load detected by said load detection mechanism.

18. The body weight support device according to claim 1, 12 or 14, wherein a portion where said body weight support force is given to said user through said leg link part and a portion where a load of said user in said body attachment part is loaded are positioned within substantially the same vertical plane.

19. The body weight support device according to claim 1, 12 or 14 that further comprises a leg link part behavior detection mechanism for detecting a behavior of said leg link part,
wherein said control unit drives said actuator, based on the behavior detected by said leg link part behavior detection mechanism.

20. The body weight support device according to claim 1, 12 or 14, wherein said floor contact part is a foot attachment part attached to a foot of said user.

21. A computer program, embodied on a non-transitory computer readable medium, the computer program configured to control a processor to perform a process, comprising:
outputting an instruction to drive an actuator so that a leg link part gives a body weight support force to a user through a body attachment part, in order to control a body weight support device that comprises said body attachment part attached to a body of said user, a floor contact part provided contactably on a floor, the leg link part for connecting said body attachment part to said floor contact part through a joint part including a knee joint part, and said actuator for driving said joint part to produce the body weight support force,
wherein said instruction drives said actuator to produce rotational power at the knee joint part, so that said leg link part gives the body weight support force to said user through said body attachment part, the body weight support force being a force for partially supporting weight of the user,
wherein the leg link part is provided not to exert the body weight support force directly on the upper or lower thighs or crotch joints of the user while the user is wearing said body weight support device,
wherein the instruction drives the leg link part so as to bend at the knee joint part in only one direction, when the user wears the body weight support device, and
wherein the instruction drives the actuator in such a way that the leg link part is not stretched, while the user is wearing the body weight support device
wherein the instruction drives the actuator so as to adjust the upper thigh, knee joint part, and lower thigh in length to prevent the upper thigh and lower thigh from becoming in line and bending to a reverse side.

22. The computer program according to claim 21 further comprising determining whether or not a leg of said user has come in contact with a floor, based on a detection result of a floor contact detection mechanism, wherein said body weight support device further comprises said floor contact detection mechanism for detecting contact between the leg of said user and the floor, and wherein if said floor contact determination unit determines that the leg of said user has come in contact with the floor, said instruction drives said actuator so as to give the body weight support force to said user.

23. The computer program according to claim 21, wherein if said floor contact determination unit determines that a leg of said user is not contact with a floor, said instruction terminates driving of said actuator and makes said joint part rotation-free.

24. The computer program according to claim 21,
wherein the body weight support device further comprises a leg link part behavior detection mechanism for detecting a behavior of the leg link part, and further comprising
predicting that the contact between the floor and the leg of the user is to be released based on the detection result of the leg link part behavior detection mechanism, and decreasing the body weight support force produced by the leg link part, before the leg of the user comes off the floor.

25. The computer program according to claim 21,
wherein the body weight support device further comprises:
a floor contact detection mechanism for detecting contact between a floor and the leg of the user, and
further comprising
predicting that the contact between the floor and the leg of the user is to be released based on the detection results of the floor contact detection mechanism and the leg link part behavior detection mechanism, and decreasing the body weight support force produced by the leg link part, before the leg of the user comes off the floor.

26. A computer program, embodied on a non-transitory computer readable medium, the computer program configured to control a processor to perform a process, comprising:
outputting an instruction to drive an actuator so that a leg link part gives a body weight support force to a user through a body attachment part, in order to control a body weight support device that comprises said body attachment part attached to a body of said user, a floor contact part provided contactably on a floor, the leg link part for connecting said body attachment part to said floor contact part through a joint part including a knee joint part, and said actuator for driving said joint part to produce the body weight support force,
wherein said instruction drives said actuator to produce rotational power at the knee joint part, so that said leg link part gives the body weight support force to said user through said body attachment part, the body weight support force being a force for partially supporting weight of the user,
wherein the leg link part is provided not to exert the body weight support force directly on the upper or lower thighs or crotch joints of the user while the user is wearing said body weight support device, and
wherein the instruction drives the leg link part so as to bend at the knee joint part in only one direction, when the user wears the body weight support device; and
determining, by a floor contact determination unit, whether or not a leg of said user has come in contact with a floor, based on a detection result of a floor contact detection mechanism, wherein said body weight support device further comprises said floor contact detection mechanism for detecting contact between the leg of said user and the floor, and wherein if said floor contact determination unit determines that the leg of said user has come in contact with the floor, said instruction drives said actuator so as to give the body weight support force to said user, and wherein said body weight support device further comprises a crotch joint part actuator for driving, as said actuator, a crotch joint part provided in said leg link part, and wherein if said floor contact determination unit determines that a leg of said user is not contact with a floor, said instruction drives said crotch joint part actuator so as to assist an upper thigh of said user to swing forward, wherein the instruction drives the actuator so as to adjust the upper thigh, knee joint part, and lower thigh in length to prevent the upper thigh and lower thigh from becoming in line and bending to a reverse side.

27. A computer program, embodied on a non-transitory computer readable medium, the computer program configured to control a processor to perform a process, comprising:

outputting an instruction to drive an actuator so that a leg link part gives a body weight support force to a user through a body attachment part, in order to control a body weight support device that comprises said body attachment part attached to a body of said user, a floor contact part provided contactably on a floor, the leg link part for connecting said body attachment part to said floor contact part through a joint part including a knee joint part, and said actuator for driving said joint part to produce the body weight support force, wherein said instruction drives said actuator to produce rotational power at the knee joint part, so that said leg link part gives the body weight support force to said user through said body attachment part, the body weight support force being a force for partially supporting weight of the user, wherein the leg link part is provided not to exert the body weight support force directly on the upper or lower thighs or crotch joints of the user while the user is wearing said body weight support device, and wherein the instruction drives the leg link part so as to bend at the knee joint part in only one direction, when the user wears the body weight support device;

determining, by a floor contact determination unit, whether or not a leg of said user has come in contact with a floor, based on a detection result of a floor contact detection mechanism, wherein said body weight support device further comprises said floor contact detection mechanism for detecting contact between the leg of said user and the floor, and wherein if said floor contact determination unit determines that the leg of said user has come in contact with the floor, said instruction drives said actuator so as to give the body weight support force to said user; and memorizing a predetermined value of the target body weight support force, wherein if said floor contact determination unit determines that a leg of said user has come in contact with a floor, said instruction drives said actuator so that said leg link part gives said target body weight support force to said user, wherein said body weight support device further comprises a load detection mechanism for detecting a load of said user on said leg link part through said body attachment part, wherein the load detection mechanism presets a lower value and an upper value of the target body weight support force, said target body weight support force has a lower limit value and upper limit value thereof, and said instruction drives said actuator so that the body weight support force by said leg link part falls between said lower and upper limit values of said target body weight support force, based on the load detected by said load detection mechanism.

28. The computer program according to claim 27, further comprising memorizing a weight of said user and as a target assist force calculation unit calculate a target body weight support force having a predetermined ratio of the weight of said user, based on said weight.

29. The computer program according to claim 21, 26 or 27, wherein said body weight support device further comprises a load detection mechanism for detecting a load of said user on said leg link part through said body attachment part, and wherein said instruction drives said actuator, based on the load detected by said load detection mechanism.

30. The computer program according to claim 21, 26 or 27, wherein said body weight support device further comprises a leg link part behavior detection mechanism for detecting a behavior of said leg link part, and wherein said instruction drives said actuator, based on the behavior detected by said leg link part behavior detection mechanism.

* * * * *